United States Patent
Pan et al.

(10) Patent No.: US 10,517,543 B2
(45) Date of Patent: Dec. 31, 2019

(54) MULTIRESOLUTION ITERATIVE RECONSTRUCTION FOR REGION OF INTEREST IMAGING IN X-RAY CONE-BEAM COMPUTED TOMOGRAPHY

(71) Applicants: The University of Chicago, Chicago, IL (US); Toshiba Medical Systems Corporation, Otawara-shi (JP)

(72) Inventors: Xiaochuan Pan, Chicago, IL (US); Zheng Zhang, Chicago, IL (US); Dan Xia, Chicago, IL (US); Yu-Bing Chang, Albany, NY (US); Joseph Manak, Albany, NY (US)

(73) Assignees: The University of Chicago, Chicago, IL (US); Canon Medical Systems Corporation, Otawara-shi (JP)

( * ) Notice: Subject to any disclaimer, the term of this patent is extended or adjusted under 35 U.S.C. 154(b) by 257 days.

(21) Appl. No.: 15/703,760

(22) Filed: Sep. 13, 2017

(65) Prior Publication Data
US 2019/0076101 A1   Mar. 14, 2019

(51) Int. Cl.
*A61B 6/03* (2006.01)
*A61B 6/00* (2006.01)
(Continued)

(52) U.S. Cl.
CPC ............ *A61B 6/032* (2013.01); *A61B 6/4085* (2013.01); *A61B 6/469* (2013.01); *G06T 3/40* (2013.01);
(Continued)

(58) Field of Classification Search
CPC ....... A61B 6/032; A61B 6/4085; A61B 6/469; A61B 6/5258; G06T 11/006; G06T 2211/424; G06T 2211/432; G06T 3/40
See application file for complete search history.

(56) References Cited

U.S. PATENT DOCUMENTS

| | | |
|---|---|---|
| 6,768,782 B1 | 7/2004 | Hsieh et al. |
| 8,625,870 B2 | 1/2014 | Zamaytin et al. |
| 2006/0061570 A1 | 3/2006 | Cheryauka et al. |
| 2008/0240335 A1* | 10/2008 | Manjeshwar .......... A61B 6/032 378/4 |

(Continued)

OTHER PUBLICATIONS

Frank Dennerlein, et. al., "Region-of-interest reconstruction on medical C-arms with the ATRACT algorithm," SPIE 8313, Medical Imaging 2012: Physics of Medical Imaging.

(Continued)

*Primary Examiner* — Michael C Bryant
(74) *Attorney, Agent, or Firm* — Oblon, McClelland, Maier & Neustadt, L.L.P.

(57) ABSTRACT

A method and apparatus is provided to generate a multiresolution image having at least two regions with different pixel pitches. The multiresolution image is reconstructed using projection data having various pixel pitches corresponding to the pixel pitches of the multiresolution image. By using a higher resolution inside regions of interest (ROIs) in both the image and projection domains and lower resolution outside the ROIs, fast image reconstruction can be performed while avoiding truncation artifacts, which result imaging is limited to an ROI excluding attenuation regions. Further, those regions of greater clinical relevance and greater structural variance within the reconstructed images can be selected to be within the ROIs to improve the clinical benefit of the multiresolution image. The multiresolution image can be reconstructed using an iterative reconstruction method in which the high- and low-resolution regions are uniquely evaluated.

20 Claims, 16 Drawing Sheets

(51) Int. Cl.
*G06T 11/00* (2006.01)
*G06T 3/40* (2006.01)
(52) U.S. Cl.
CPC .......... *G06T 11/006* (2013.01); *A61B 6/5258* (2013.01); *G06T 2211/424* (2013.01); *G06T 2211/432* (2013.01)

(56) References Cited

U.S. PATENT DOCUMENTS

| | | | |
|---|---|---|---|
| 2013/0051519 A1 | 2/2013 | Yang et al. | |
| 2016/0242721 A1 | 8/2016 | Zou et al. | |
| 2019/0076101 A1* | 3/2019 | Pan | A61B 6/032 |

OTHER PUBLICATIONS

Clemens Maaß, et al, "New approaches to region of interest computed tomography," Medical Physics, vol. 38, issue 6, p. 2868-2878, Jun. 2011.

Zhang, et al., "Reconstruction with Variable Resolution in C-arm Cone-beam CT,"Z. The 12th International Meeting on Fully Three-Dimensional Image Reconstruction in Radiology and Nuclear Medicine, pp. 372-375.

Qian Cao, et al., "Multi-Resolution Penalized Weighted Least-Squares Reconstruction for Quantitative Cone-Beam CT Imaging of Bone Morphology" , Fully 3D Conference, Jun. 1-3 2015, (4 pages).

Alexander A. Zamyatin, "Multi-Scale Iterative Reconstruction," 2011 IEEE Nuclear Science Symposium Conference Record, MIC21.S-111, Nov. 15, 2011, pp. 4152-4154.

Zheng Zhang, et al., "Iterative Image Reconstruction with Variable Resolution in CT," 2011 IEEE Nuclear Science Symposium Conference Record, MIC21.S-114, pp. 4155-4157.

Dang et al., "Multi-Resolution Statistical Image Reconstruction for Mitigation of Truncation Effects: Application to Cone-Beam CT of the Head," Institute of Physics and Engineering in Medicine Physics in Medicine & Biology, Dec. 29, 2016, vol. 62, No. 2.

Costin et al., "A Multi-Resolution Image Reconstruction Method in X-Ray Computed Tomography," Journal of X-Ray Science and Technology, IOS Press, 2011, 19 (2), pp. 229-247.

* cited by examiner

MULTIRESOLUTION ITERATIVE RECONSTRUCTION FOR REGION OF INTEREST IMAGING IN X-RAY CONE-BEAM COMPUTED TOMOGRAPHY

FIELD

This disclosure relates to reconstructing images in computed tomography (CT) using various regions of different resolution in the image domain and corresponding regions of different resolution in the sinogram/projection domain, and, more particularly, to selecting the regions of high resolution in the image and sinogram/projection domains to correspond with regions of high spatial frequencies and/or regions identified to have clinical significance.

BACKGROUND

Computed tomography (CT) systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation transmitted through the body is measured by processing electrical signals received from the detector.

A CT sinogram indicates attenuation through the body as a function of position along a detector array and as a function of the projection angle between the X-ray source and the detector array for various projection measurements. In a sinogram, the spatial dimensions refer to the position along the array of X-ray detectors. The time/angle dimension refers to the projection angle of X-rays, which changes as a function of time during a CT scan. The attenuation resulting from a portion of the imaged object (e.g., a vertebra) will trace out a sine wave around the vertical axis. Those portions farther from the axis of rotation correspond to sine waves with larger amplitudes, and the phases of the sine waves correspond to the angular positions of objects around the rotation axis. Performing an inverse Radon transform—or any other image reconstruction method—reconstructs an image from the projection data in the sinogram.

In clinical applications, a given sub-region within the body might have greater importance for a particular scan of a particular patient. For example, in interventional CT, a stent or other medical device might be inserted into a patient, and the region immediately surrounding the placement of the medical device is of primary importance. To achieve higher resolution in this area, a smaller diameter X-ray beam can be focused on the relevant region of interest for a CT scan. However, the reconstructed image from this smaller region of interest can result in truncation error. On the other hand, a reconstructed image with a larger field of view will either result in poorer resolution or require significantly more time and computational resources to reconstruct from the projection data.

In a CT scan, truncation error and artifacts result when a small diameter X-ray beam occupies less than the entire cross-section of a patient. Since incomplete data is available outside the region of interest (ROI) illuminated by the X-ray beam, the reconstruction can suffer from severe artifacts potentially rendering the image useless. Different approaches have been proposed to reduce these artifacts by estimating or determining data outside the ROI.

For example, a first category of algorithms attempts to overcome the ROI artifact by estimating the data outside the ROI. A technique can be used to extrapolate the truncated data. In some implementations, the extrapolation procedure can be incorporated into the convolution step of a filtered back-projection (FBP), or by using a smooth function to improve reconstruction inside the ROI. These estimated or eliminated projections may not model the objects outside the ROI accurately, resulting in residual artifacts. Moreover, these techniques do not provide image information outside the ROI, which image information can provide visual context for the image in the ROI, making it easier for clinical practitioners to interpret the reconstructed image.

Certain other methods of solving the truncation artifact problem use two passes, a first pass corresponding to a full field of view and a second pass using a limited or restricted field of view. For example, ROI image reconstruction can be performed by using iterative reconstruction (IR) by using two-pass IR and one projection subtraction in-between the two passes. Two options for implementing this method are: (i) a coarse grid size is applied in the first pass and a fine grid size is applied in the second pass; and (ii) a fine grid size is used in both passes, but a shrunken image volume is applied in the second-pass by reducing number of voxels. The two-pass method can decrease the truncation artifact, but at the cost of increased complexity and time to perform the second scan and perform additional reconstruction steps.

These extrapolation methods and two-pass methods fail to sufficiently mitigate the truncation artifact without increasing the computational time to reconstruct an image. However, increasing the computational time is not feasible in certain clinical applications when clinical practitioners rely on rapid feedback based in the imaging for task, such as positioning and arranging a stent or a medical device in a patient. Thus, an improved method of multiscale imaging is desired.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
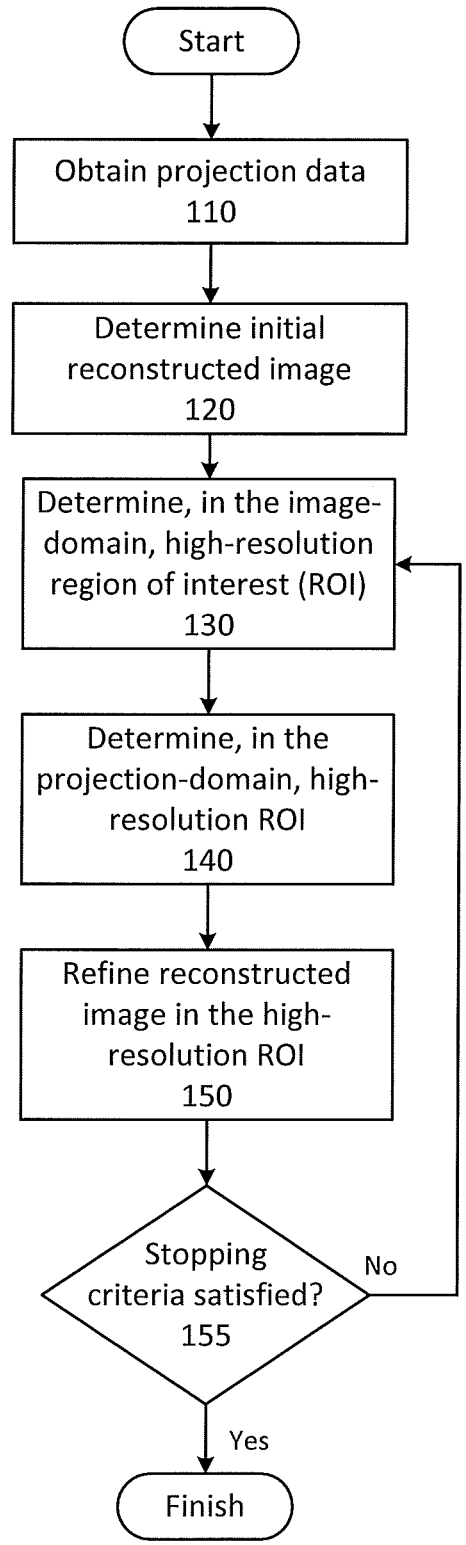
FIG. 1 shows a flow diagram of a first implementation of a multiresolution iterative reconstruction (IR) method, according to one implementation.

In computed tomography (CT) and cone-beam CT (CBCT), region of interest (ROI) reconstruction is used to obtain high-resolution images within a designated ROI. This technique can also be referred to as zoomed ROI reconstruction, and uses a smaller image voxel size for representation of anatomic features in the designated ROI. Further, in certain implementations, ROI reconstruction can also generate coarse-resolution images and information for regions outside the ROI. The methods and apparatus described herein provide computational and other advantages over more conventional methods by, among other things, using different pixel pitches for the projection data corresponding to regions outside the ROI relative to the pixel pitch used for regions projecting through the ROI. In contrast, more conventional methods do not use multiple pixel pitches within the projection data for a single CT scan. Further, methods described herein perform ROI reconstruction using iterative reconstruction based on a single scan, rather than multiple scans such as are used in a two-pass method.

Often for CT using iterative reconstruction (IR), the entire imaged object OBJ is within the image volume of the CT scanner. This reduces the truncation effect. However, when high-resolution images are being reconstructed, decreasing the imaged region to a small ROI can reduce the computational burden for reconstructing an image of the object OBJ. Otherwise the time required to reconstruct a high-quality image can become prohibitive, especially when high-resolution reconstruction for the ROI is desired, and the same high-resolution is used for the entire volume of the reconstructed image.

The computational time for iterative image reconstruction is often dominated by the forward-projection operations and back-projection operations. This is because often IR algorithms converge to the reconstructed image using multiple steps of iteration, and each step can include both a forward-projection operation and a back-projection operation. The number of floating point operations for each of these operations can be of the order of the number of voxels in the image domain times the number of pixels in the projection/sinogram domain. As used herein, the terms "sinogram domain" and "projection domain" are used interchangeable. Thus, doubling the resolution without changing the size of the image or projection domains can result in a $2^5=32$ times increase in the computational time for each forward- and back-projection operation.

Accordingly, for a large image volume with fine resolution the computational complexity can escalate rapidly, which is why for clinical applications in which high resolution is desired for the ROI, minimizing the ROI is advantageous. However, as mentioned above, when the ROI excludes portions of the object, truncation artifacts result from the unknown X-ray attenuation attributable to those portions of the object excluded from the imaging region.

Full field-of-view (FOV) projection data can be used to provide information regarding the X-ray attenuation for those regions of the object OBJ excluded from the ROI, thus eliminating truncation artifacts. Accordingly, if the full FOV is represented in the projection data, the entire object OBJ is represented in the forward-projection and back-projection operations in IR, and the truncation effects are reduced. In high-resolution imaging such as cone beam CT (CBCT) used in interventional radiology, the native detector resolution for the projection data can be rather high, i.e., a small pixel pitch, which is defined as the distance between nearest neighbour pixels.

Full FOV projection data with native detector resolution could impose a high computational burden, especially when only a small ROI in the image domain requires the highest resolution possible based on the native resolution. Thus, full FOV images can be reconstructed by down sampling the projection data from the native resolution to a coarser detector resolution (i.e., larger pixel pitch). This downsampling can be achieved, for example, by grouping the pixels into groups corresponding to larger pixels (e.g., 2-by-2 squares including four native pixels, or 2-by-3 rectangles including six native pixels) and summing or averaging over the intensity/count value for the respective native pixels in each grouping of native pixels to determine the downsampled projection data corresponding to the coarse-resolution pixels.

Alternatively, any size, shape, and dimension of coarse projection data can be obtained by mapping from the native resolution grid to a coarse-resolution grid using any known interpolation, extrapolation, and/or integration method. Downsampling the projection data by a pixel-pitch ratio of 2 with a commensurate change to the image-domain resolution can result in a factor of $2^5=32$ decrease in the computational time to perform the forward-projection and back-projection operations, resulting in a drastic increase in efficiency for the IR algorithm.

To achieve both fast image reconstruction with the full FOV while also achieving high resolution within a ROI, the image domain can be partitioned into a low-resolution region outside of the ROI and a high-resolution region inside of the ROI, as described in U.S. Pat. No. 8,625,870, incorporated herein by reference in its entirety. However, the efficiency of the IR algorithm can be further enhanced by not only partitioning the image domain into high- and low-resolution regions, but also partitioning the sinogram domain, i.e., the projection data, into high- and low-resolution regions. Returning to the example in which downsampling is performed by a factor of two change in the pixel pitch, changing the pixel pitch of voxels only (voxels are volume pixels in the image domain) only decreases the computational burden by a factor of $2^3=8$. The total improvement by a factor of $2^5=32$ requires both the voxels in the image domain and the pixels in the projection data be downsampled by a pixel-pitch ratio of two.

Referring now to the drawings, wherein like reference numerals designate identical or corresponding parts throughout the several views, FIG. 1 shows flow diagram of an IR method using downsampled regions in both the image and sinogram domains for pixels and voxels outside of the ROI.

Figure 2:
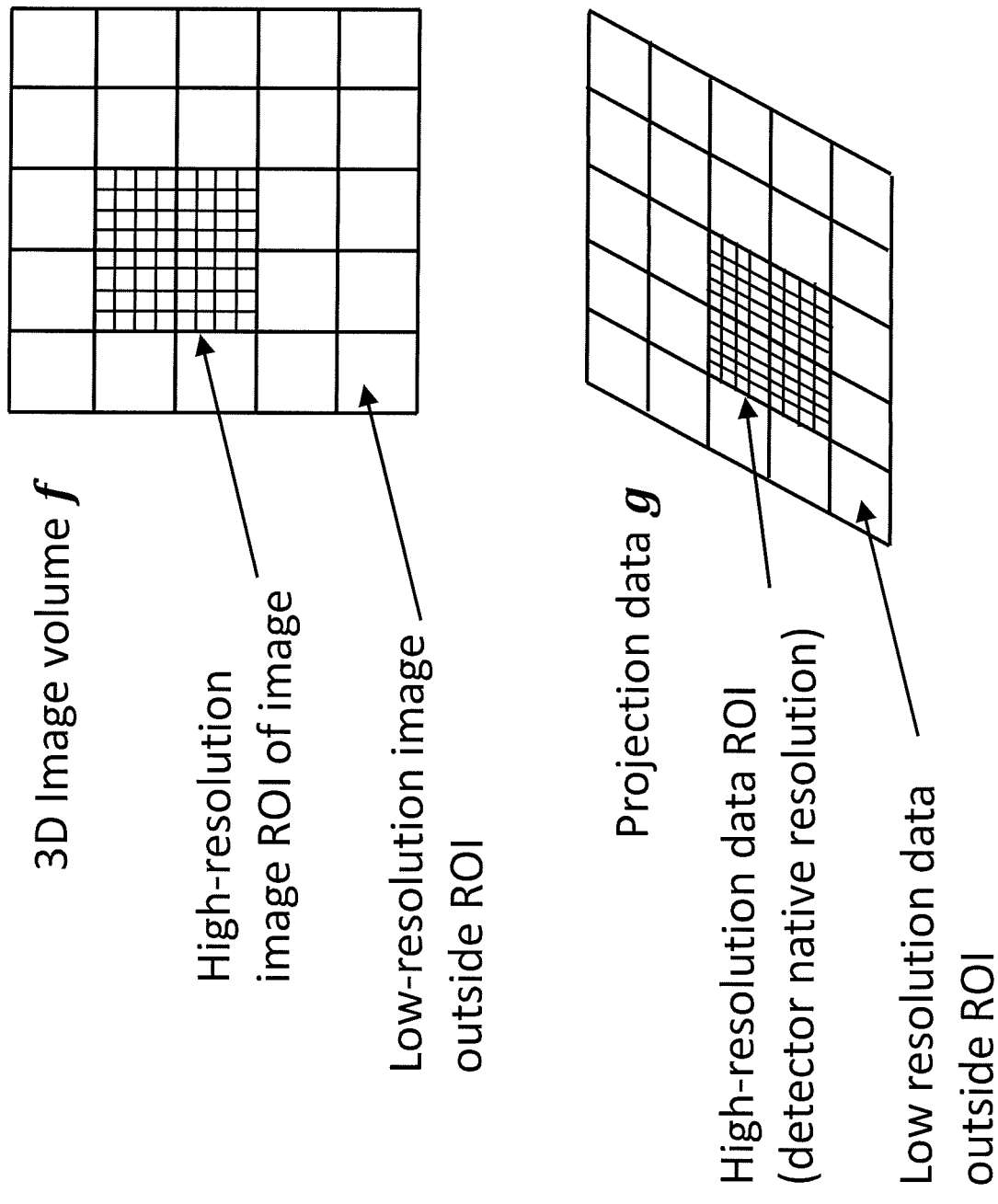
FIG. 2 shows high-resolution and low-resolution regions within projection data and within a reconstructed image generated from the projection data, according to one implementation.

FIG. 2 shows an example in which both the voxels in the image domain and the pixels in the projection data are at a native resolution in regions corresponding to the ROI and are downsampled by a pixel-pitch ratio of 4 for regions outside the ROI. For simplicity, FIG. 2 shows only a single high-resolution (HR) region in the image and sinogram domains. In general, multiple high-resolution ROIs can be selected within the full FOV, as discussed later. Further, the resolution for each ROI can be separately specified in accordance with the type of anatomic features represented in the ROI and the desired resolution for the given clinical application. To obtain multiple high-resolution ROIs, as discussed herein, the higher resolution within the respective ROIs can be achieved by initializing the entire FOV at a low resolution for both voxels and pixels and then imposing the finer resolution in the projection domain and iteratively solving the IR algorithm to refine the resolution in the image domain. When more than one ROI is designated in the full FOV, the improved resolution within the ROIs can be achieved serially or in parallel as discussed herein. In serial, the switch from coarse to fine resolution in both the sinogram and image domains is performed in series for each of the respective ROIs, such that the resolution of a current ROI is refined through the IR method before moving onto the next ROI and refining the resolution in the next ROI using the IR method. In parallel, the resolution for all of the ROIs is refined simultaneously.

Returning to FIG. 1, method 100 performs a multiresolution reconstruction of an object OBJ.

In step 110 of method 100, the projection data is obtained. This projection data can be obtained by performing a CT scan using a CT scanner such as the CT scanner described herein. Also, the projection data can be obtained by recalling from computer memory projection data that has been previously obtained. The obtained projection data can be at the native resolution of the X-ray detectors of the CT scanner.

In step 120 of method 100, an initial reconstructed image can be determined. The initial image can be generated using downsampled projection data and using an image resolution for the initial image that is commensurate with the downsampled projection data. The initial image can be generated using any known CT reconstruction method, including filtered back-projection (FBP), a Feldkamp-Davis-Kress (FDK) reconstruction method, and an IR method using, e.g., using an objective function with a least-squares or a penalized-weighted-least-squares data-fidelity term and a regularization term. In certain implementations using an IR method, the IR method can be performed for a predefined number of iterations, rather than being performed until convergence. The IR method can also use various acceleration and other techniques to improve convergence, including, e.g., ordered subsets, Nesterov's acceleration, and separable quadratic surrogates. Further, the IR method can be initialized using a FBP or FDK reconstructed image. Various combinations of CT reconstruction can also be used, as would be understood by a person of ordinary skill in the art.

As discussed above, the down-sampling of the projection data can be achieved by grouping the fine-resolution pixels into pixel groups corresponding to the coarse-resolution pixels of the downsampled data, and then averaging or summing the values of the respective pixel groups of the fine-resolution pixels to generate the values of the coarse-resolution pixels. Alternatively, the fine-resolution pixels can be resampled onto a grid or other pixel pattern for the coarse-resolution pixels using interpolation, extrapolation, and/or integration from the fine-resolution grid onto the coarse-resolution grid.

In step 130 of method 100, an ROI can be determined within the initial image. The ROI can be a region in which high-resolution image reconstruction is desired. The process for determining the ROI can be automated or include user input, e.g., using a graphical user interface (GUI), to determine features and or regions of clinical relevance. For example, automated determination of the ROI can include using an edge-detection method to determine regions having a high degree of high-spatial-frequency (HF) content, such as at boundaries between organs and bone. These high-frequency regions benefit more from high-resolution image reconstruction than regions with more uniform low-spatial-frequency (LF) content. The ROI can be a three-dimensional shape or a two-dimensional-shape that is extruded along a given length in the third dimension. In certain implementations the ROI can be determined using a threshold-and-region-growing method. Pixels corresponding to an edge or high-frequency measurement above a predefined threshold can seed the threshold-and-region-growing method.

After the various ROIs are determined with their corresponding pixel pitches, the voxel values of the initial image can be mapped using interpolation onto voxels having the desired pixel pitch within each respective ROI, as indicated in FIG. 2.

Various edge or high-frequency measurements can be used as indicia that high-resolution is appropriate for a given neighborhood of pixels. For example, an absolute value of a convolution between the initial image and a derivative function can be normalized by the average attenuation within the neighborhood of each pixel to generate a measure of the derivative. This measure of the derivative will be larger in regions of the initial image exhibiting significant spatial variations in the attenuation, indicating regions that can benefit from higher resolution.

Further, another measure of which regions can benefit from high-resolution image reconstruction can be generated using a spatially windowed standard deviation normalized by the localized mean. The normalized standard deviations provides a measure of which regions are highly textured.

Similarly, a spatially windowed and mean frequency of the power spectral density would also provide a measure of which regions are highly textured. Also, the percentage of attenuation represented by high-frequency components of a wavelet-based transformation would similarly provide a measure indicating regions benefiting from higher resolution. This is also true for other measurements based on a pyramid decomposition of the reconstructed image (e.g., a Gaussian or Laplacian pyramid decomposition or a wavelet transform decomposition). Many other measures of the regions exhibiting high spatial variations are also contemplated, as would be understood by a person of ordinary skill in the art. Any edge-detection method or method for detecting differences in texture or spatial variation/structure among different regions can be used.

In certain implementations, selection of regions of low- and high-resolution images can be determined by analyzing the initial image, such that regions of the image amenable to denoising or smoothing can be assigned a coarse resolution while remaining regions can be assigned high resolution.

Further, different regularizers can be assigned within the various regions, according to their determined statistical properties. For example, in the high-resolution regions, edge-preserving or edge-enhancing regularizers can be applied, whereas a smoothing regularizer can be applied in coarse-resolution regions. In certain implementations, all regions use the same regularizer, e.g., a total variation (TV) minimization regularizer.

In certain implementations, a dedicated GUI can be used for the selection of regions of low and high resolution within the initial image. The GUI can display the initial image, and a user can specify the ROIs of high resolution within the GUI.

Further, in certain implementations, the user can also specify the ROIs of low resolution within the GUI.

In certain implementations, segmentation into multiple resolutions can be performed automatically using prior input from a user or using defaults settings. Based on these inputs and/or default settings, criteria of image segmentation are set for the determination of the regions of high (low) resolution. Various techniques of image segmentation can be implemented based on the criteria to find targets of the high resolution regions. Those techniques can involve both automatic and semi-automatic techniques. When a semi-automatic approach is applied, a GUI can be involved so that initial seeds or cropping can be provided by the user.

In certain implementations, a Laplacian-decomposition approach can be used. In the Laplacian-decomposition approach a Laplacian filter is used as an analysis filter bank operating on the initial image, resulting in a Laplacian pyramid of the sub-band architecture. Each sub-band volume image can be processed using an interactive reconstruction, but with a scale-related pixel pitch. The reconstruction of high-frequency sub-bands, which have more details of image features, employs a smaller pixel pitch, while the low frequency sub-band reconstruction employs a coarser grid. The final output is the synthesis of the reconstructed sub-band images.

In certain implementations, a wavelet-based approach can be used. Similarly to the Laplacian-decomposition approach, a wavelet transformation can be applied to the initial image, forming a wavelet pyramid of a sub-band architecture. High-resolution features are reconstructed from the high-frequency sub-bands by using finer resolution grids, while low-resolution regions are reconstructed from the low-frequency sub-bands.

Figure 3:
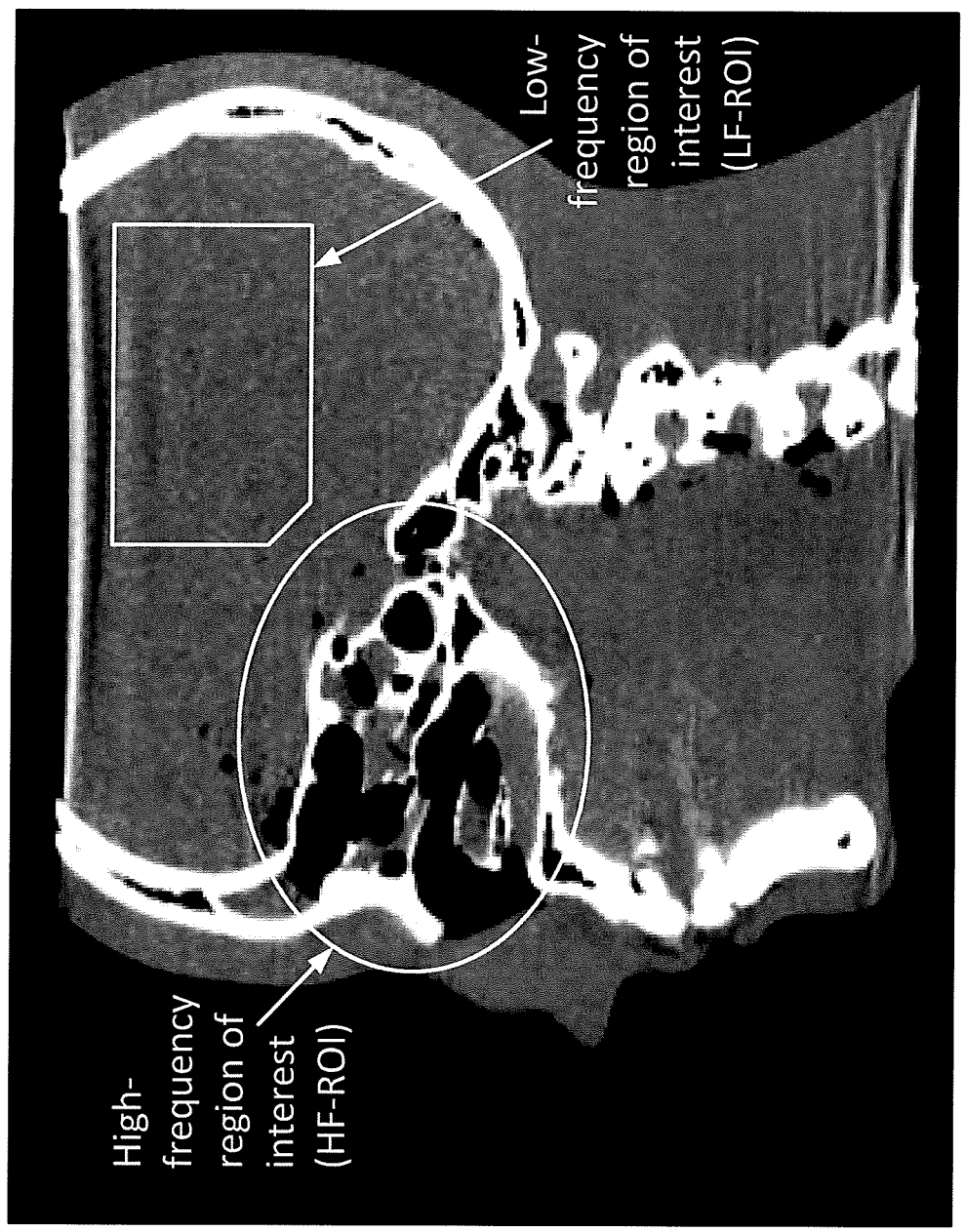
FIG. 3 shows an example of a reconstructed image in which a low-frequency and a high-frequency region of interest (ROI) have been superimposed on the reconstructed image, according to one implementation.

FIG. 3 shows a cross-section of a reconstructed image in which an HF ROI is designated. Also, FIG. 3 shows a LF ROI, which uses coarser resolution than the HF ROI. Method 100 is not limited to only two levels of resolution, but multiple resolutions can be used in various regions. For example, a high resolution can be applied for regions designated as clinically relevant or designated as HF ROIs, whereas a medium resolution can be applied in undesignated regions and a low resolution can be applied in regions designated to be LF-ROIs.

Figure 4:
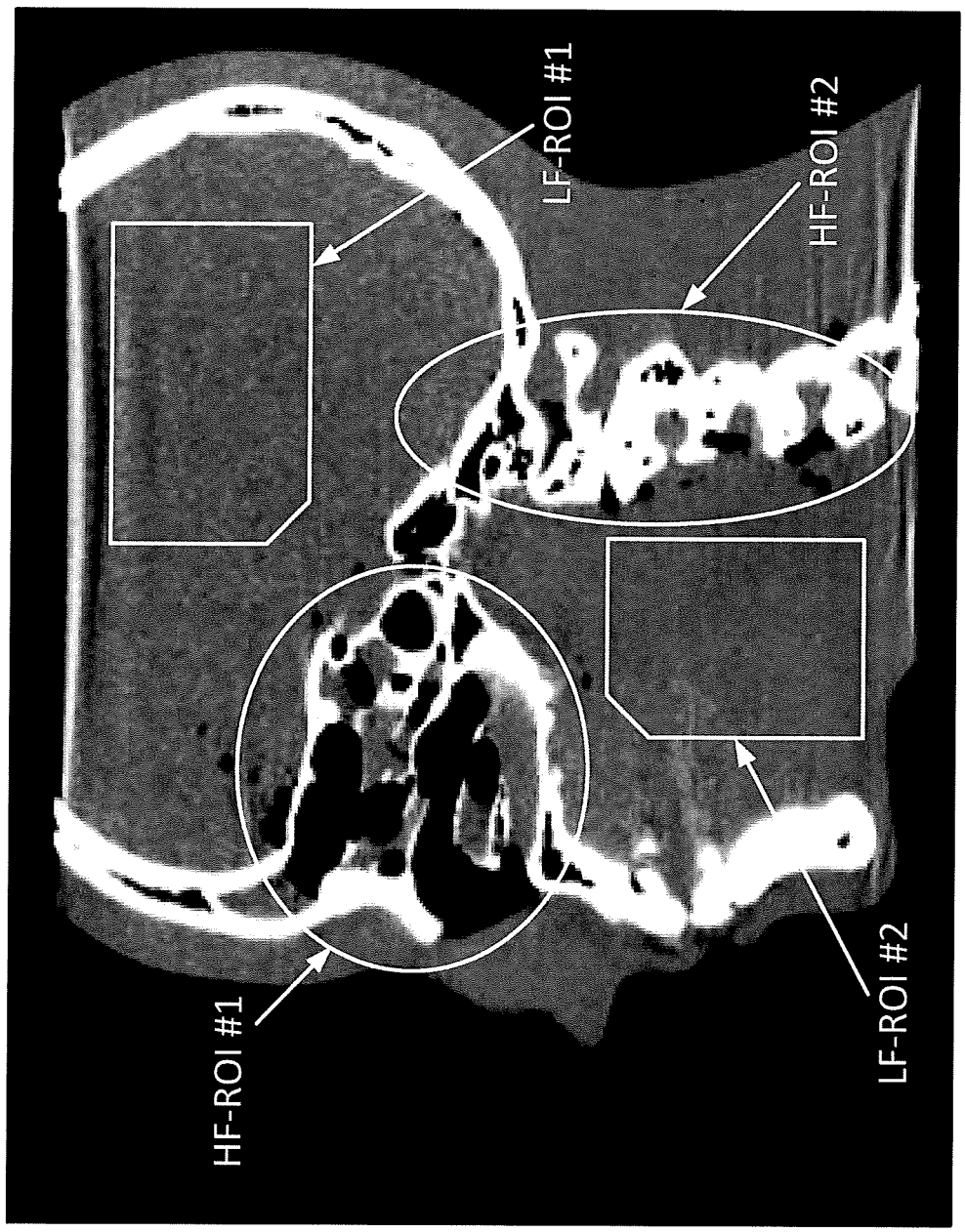
FIG. 4 shows an example of a reconstructed image in which multiple low-frequency ROIs and multiple high-frequency ROIs have been superimposed on the reconstructed image, according to one implementation.

FIG. 4 shows a cross-sectional slice of a reconstructed head image in which two HF ROIs are identified and two LF ROIs are identified. The HF ROIs can have the same resolution, or they can have different resolutions. Similarly, the LF ROIs can have the same or different resolutions. Thus, multiple different resolutions can be applied. For example, the resolution within a given ROI can be tuned automatically to achieve an optimum resolution. If the rate of change (i.e., spatial derivative) of detected edges within the ROI are determined to be approximately equal to the resolution limit of the pixel pitch within the ROI, then the pixel pitch can be incrementally decreased towards the native resolution of the X-ray detectors, until the pixel pitch is sufficient to resolve the sharpest features in the HF ROI or the native resolution is reached.

In certain implementations, if the current pixel pitch within an ROI is sufficient to resolve some features but not others, a sub-ROI can be determined within the ROI, the sub-ROI corresponding to those features requiring a smaller pixel pitch. Then the smaller pixel pitch can be applied to the sub-ROI, and the IR method can be performed to refine the resolution within the sub-ROI in order to resolve the edges and fine features within the sub-ROI. Further verification and testing can be performed using the above-discussed edge and structure measurements, e.g., to determine whether the smaller pixel pitch is adequate to resolve the finest features in the sub-ROI. If even finer resolution is required to resolve these features, then the pixel pitch within the entire sub-ROI can be further decreased.

Alternatively, if some edges and features in the sub-ROI are adequately resolved within the sub-ROI while other edges and features are not, then the sub-ROI can be further sub-divided to obtain a sub-sub-ROI, and so forth until all of the features in the ROI are adequately resolved or the native resolution is reached. This iterative process can be realized by iterating through steps 130, 140, 150, and 155 until the stopping criteria are satisfied, as described below.

Figure 5:
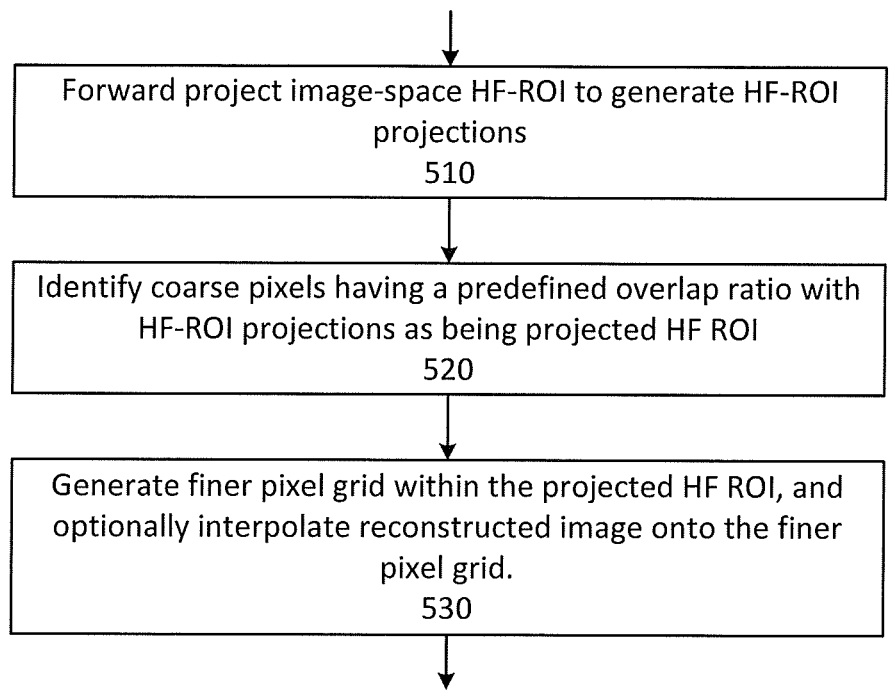
FIG. 5 shows a flow diagram of a step performing a forward projection of a high-resolution ROI in the image domain onto the projection domain, according to one implementation.
Figure 7A:
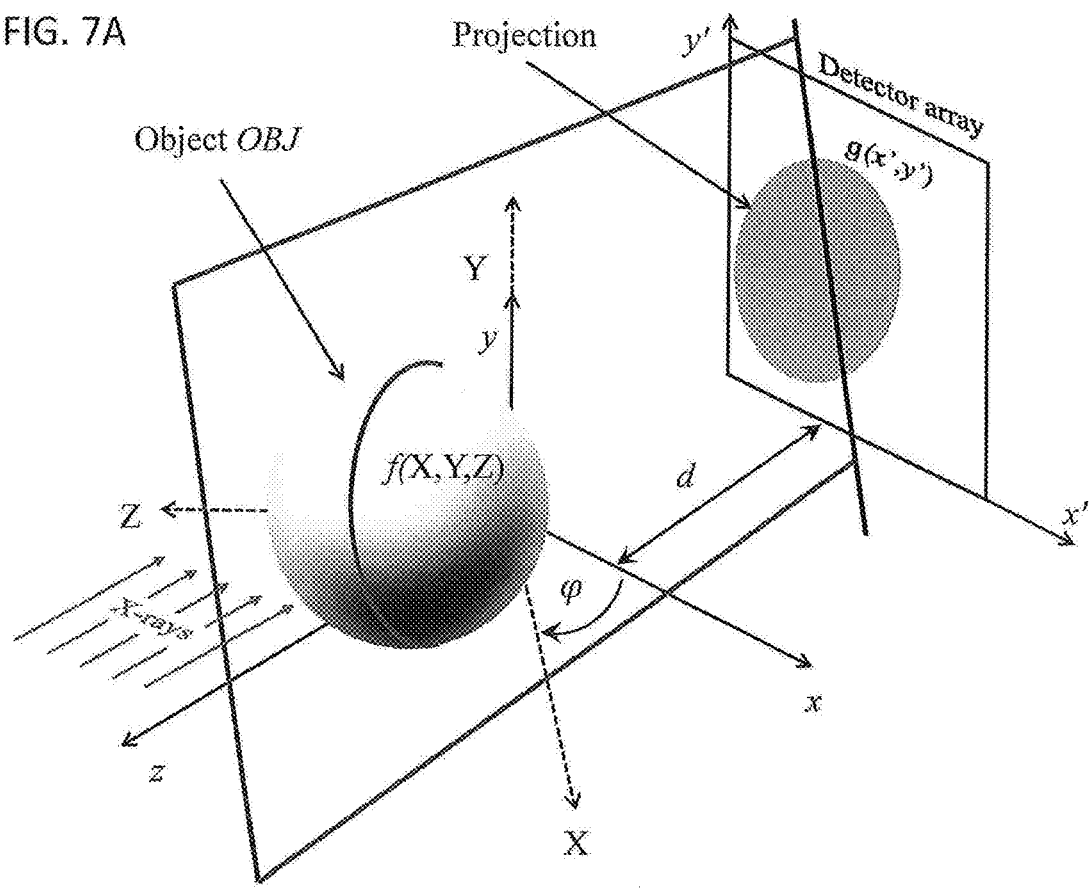
FIG. 7A shows a diagram of an example of a projection of a three-dimension object OBJ onto a two-dimensional detector array, according to one implementation.
Figure 7B:
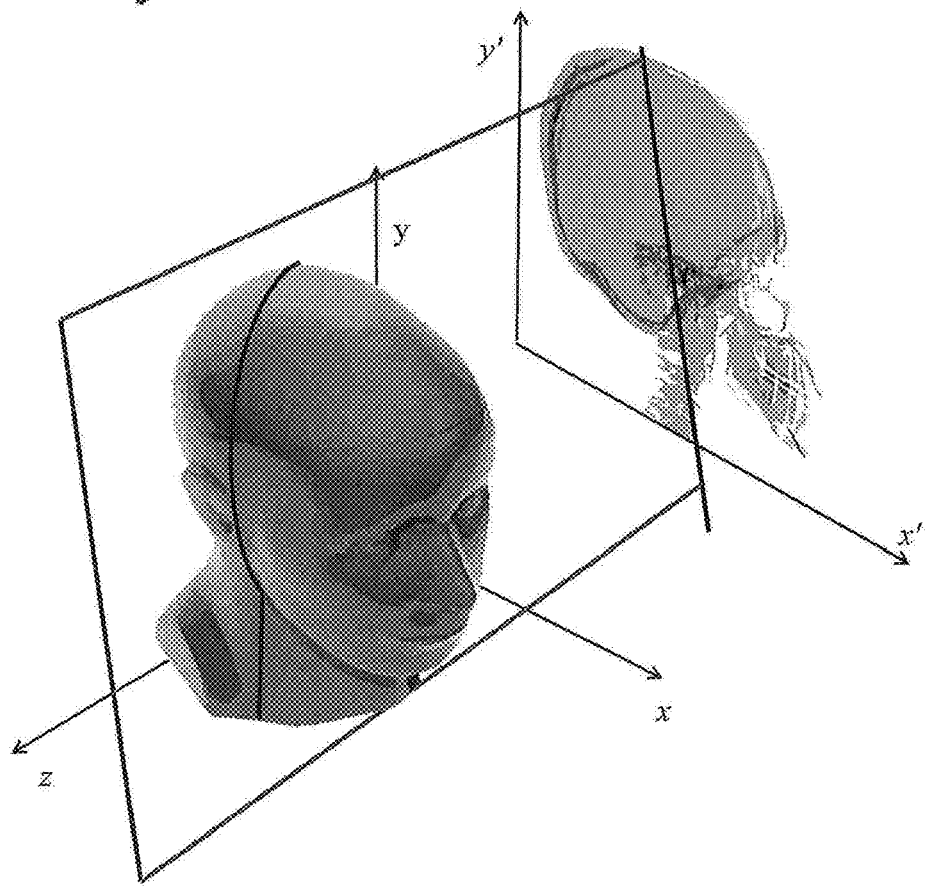
FIG. 7B shows a diagram of an example of a projection of a head phantom onto a two-dimensional detector array to generate projection data.
Figure 7C:
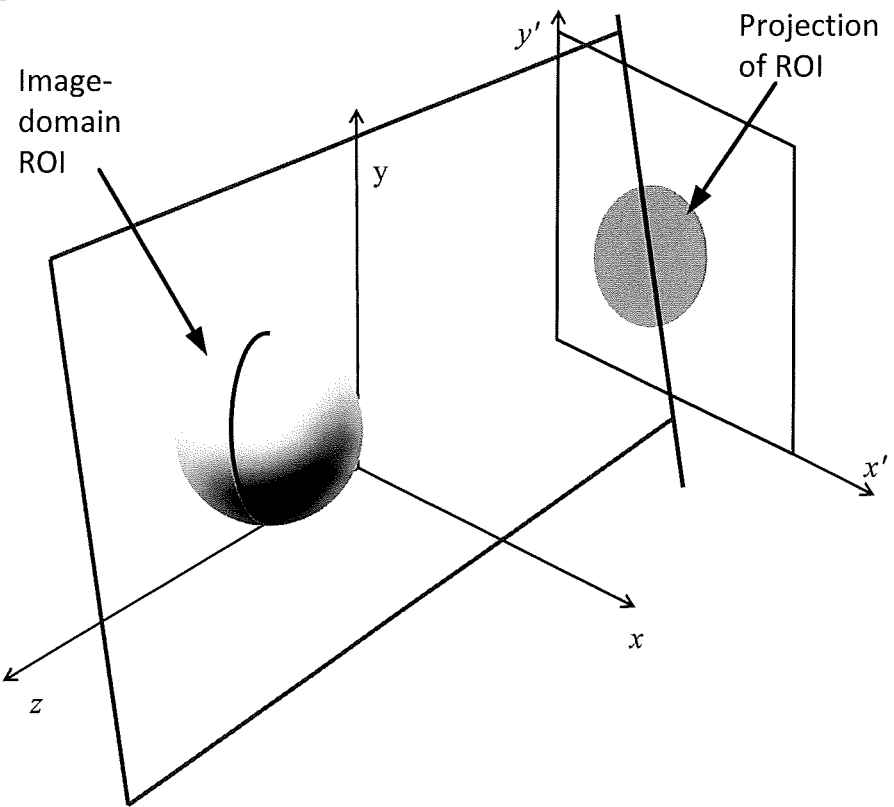
FIG. 7C shows a diagram of an example of a forward projection of an image-domain ROI onto a projection domain to determine a projection of the ROI.
Figure 7D:
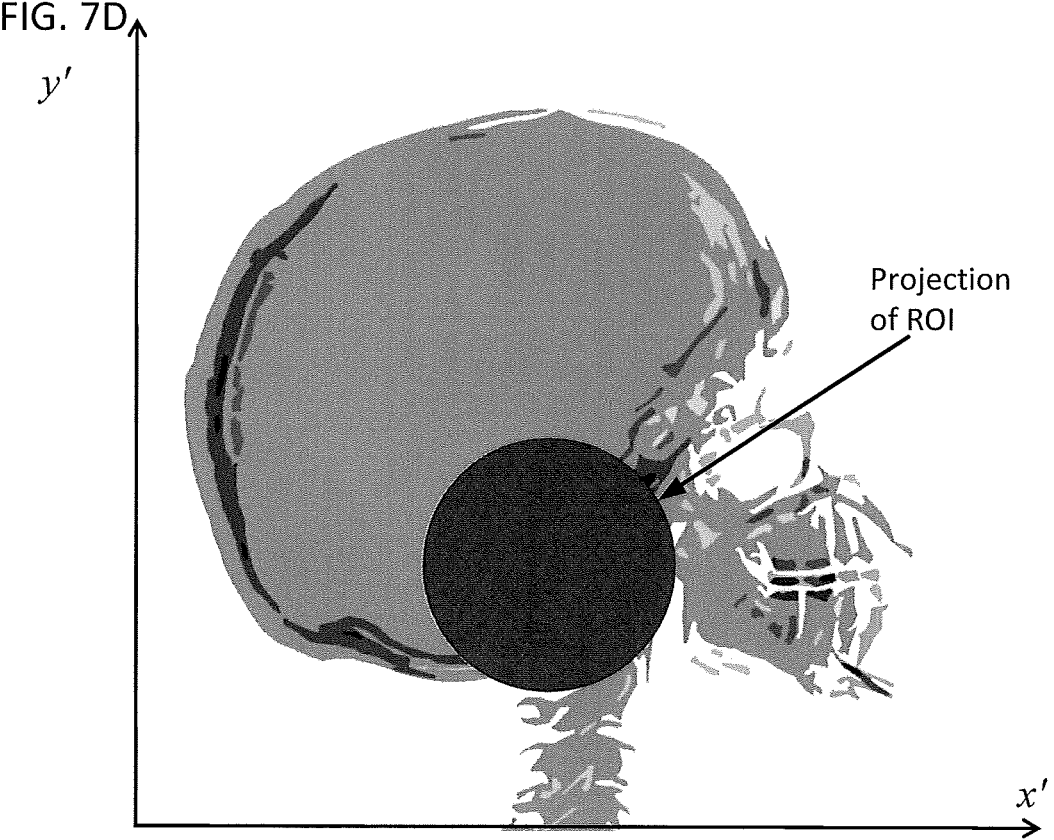
FIG. 7D shows the projection of the ROI superposed on the projection data of the head phantom.
Figure 8:
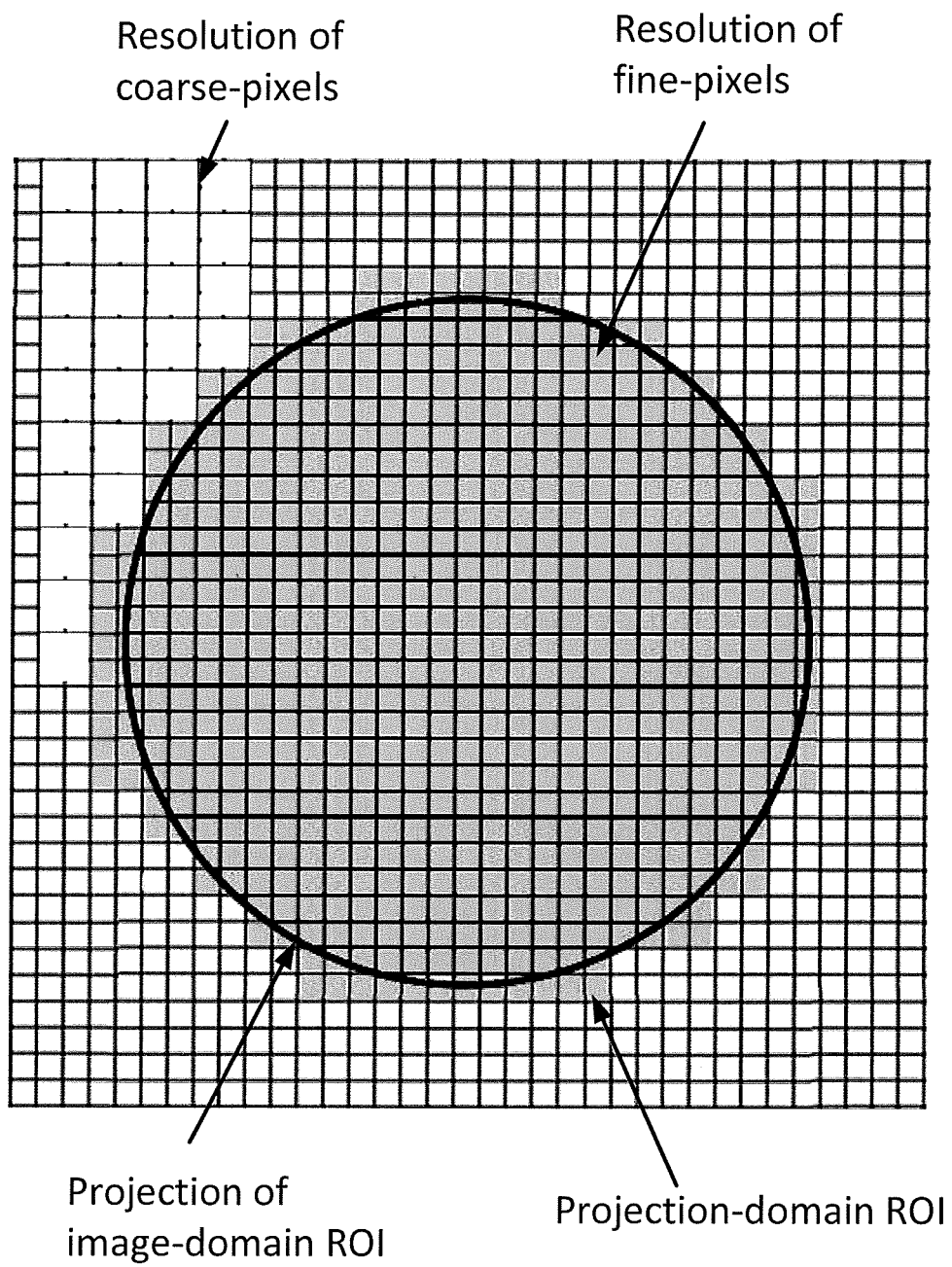
FIG. 8 shows an example of a projection-domain ROI being determined from a projection of the image-domain ROI when a ratio between the pixel pitch inside and outside the ROI is two.
Figure 9:
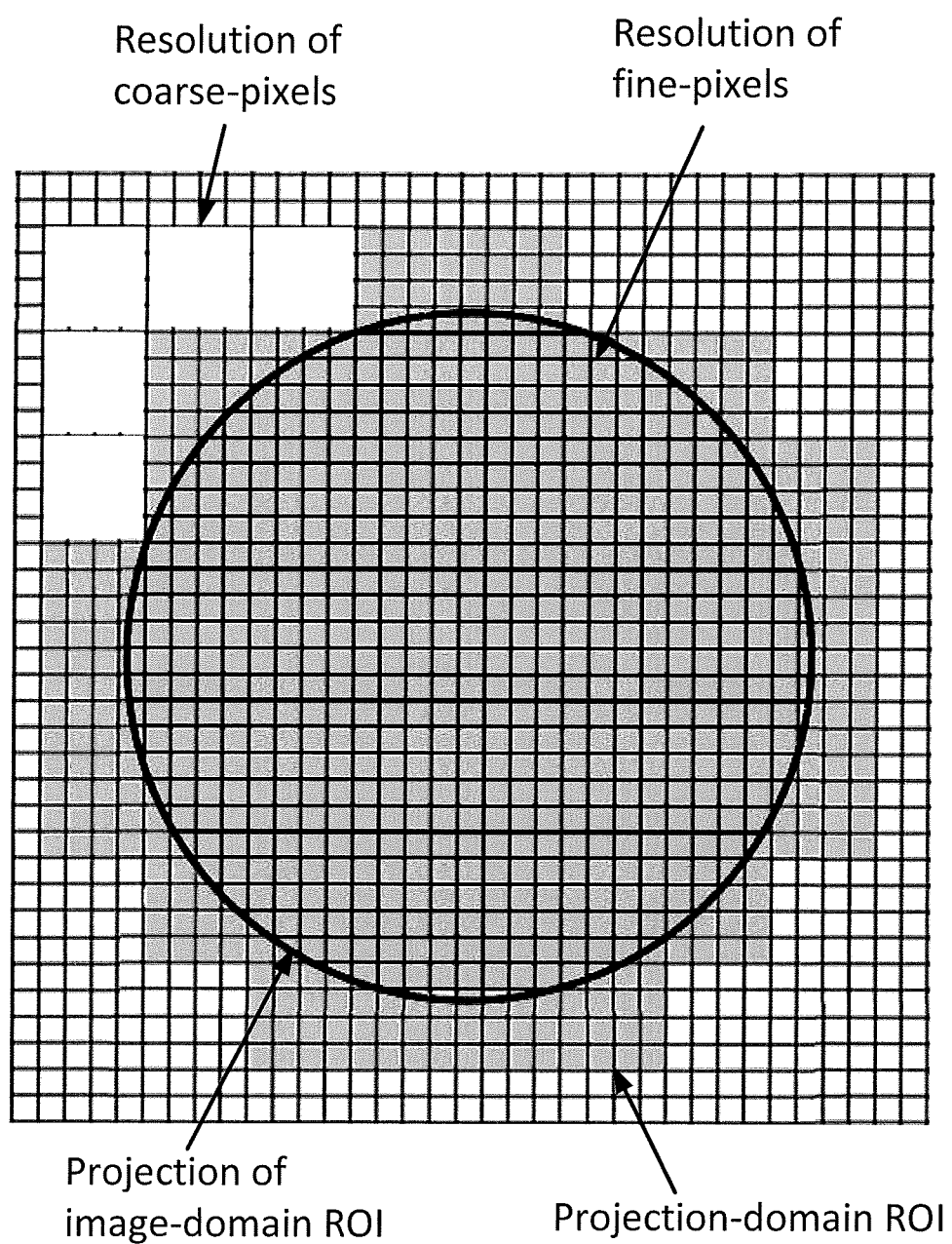
FIG. 9 shows an example of a projection-domain ROI being determined from a projection of the image-domain ROI when a ratio between the pixel pitch inside and outside the ROI is four.

In step 140 of method 100, the various ROIs in the image domain are forward projected onto the sinogram domain. FIG. 5 shows a flow diagram of one implementation of step 140 to forward project the ROIs from the image domain to the sinogram domain. Further, FIGS. 7A, 7B, 7C, and 7D illustrate the forward projection from the image domain to the sinogram domain, and FIGS. 8 and 9 illustrate determining, based on the forward projection, which pixels in the sinogram domain are in the sinogram-domain ROI, and which are out of the sinogram-domain ROI.

The reconstructed image, $f$, and the projection data, $g$, are related by the system-matrix equation $$Af=g,$$

wherein A is the forward-projection operator/matrix, representing the Radon transform or projections of the object OBJ onto the detector plane. In certain implementations, this forward-projection operator A can be referred to as the ray-driven forward projection. A corresponding pixel-driven back-projection, B, can also be defined. FIG. 7A illustrates the physical mechanism of X-rays traversing an object having a spatial profile $f$ to forward project $f$ onto a detector array, generating the projection image g. FIG. 7B shows the forward projection of a head phantom, and FIG. 7C shows a ROI corresponding to a portion of the spinal cord of the phantom being forward projected. Finally, FIG. 7D illustrates the overlap between the projection image of the phantom and the projection of the image-domain ROI onto the image domain.

FIG. 7A shows the geometry of a projective measurement for CT imaging. An object OBJ for which the X-ray attenuation as a function of position is given by the function ƒ(X,Y,Z) is positioned such that X-rays traverse the object OBJ before being detected by a detector array. An X-ray beam propagates along the z-axis, which is at a projection angle φ relative to the Z-axis. Multiple projection images are taken at several different projection angles φ. In each projection image the X-rays pass through the image object and continue to propagate until the X-rays impinge upon the detector array. The detector array can include an array of pixels to detect the X-ray intensity at discrete locations across the detector array. These measurements give rise to a map of the projected intensity/attenuation g(x',y') across the detector, which is recorded using a computer memory and later processed to create a CT image of the image object OBJ. In FIG. 7A the detector is shown to be a distance d from the closest boundary of the image volume. The axes x, y, and z define the coordinate system of the object OBJ, whereas the axes X, Y, and Z define the coordinate system of the X-ray scanner, which rotates relative to the object OBJ and x' and y' define the coordinates of the pixel array for the X-ray detector.

FIG. 7B shows generation of a projection image from a head phantom, and FIG. 7C shows a virtual projection of an image-domain ROI by forward projecting the ROI onto a projection plane corresponding to the pixels of the detector array. FIG. 7D shows a superposition of the projection of the ROI over the projection image of the head phantom. It can be observed that the projection of the ROI overlaps those pixels for which a greater pixel pitch is desired in order to generate a higher-resolution reconstructed image. On the other hand, high-resolution projection data is not needed for pixels not overlapping the projection of the ROI because these pixels correspond to low-resolution portions of the reconstructed image.

In certain implementations, the coarse-resolution pixels (i.e., the pixels outside of the sinogram-domain ROI) are determined as being those coarse-resolution pixels that do not overlap the projection of the image-domain ROI, and the ROI in the sinogram domain includes all remaining pixels of the projection data. The ROI in the sinogram-domain will have a smaller pixel pitch, as shown in FIGS. 8 and 9. In FIGS. 8 and 9, the circumference of the circle represents a projection of the image-domain ROI onto the sinogram domain. In FIG. 8 the ratio between pixel pitches inside and outside the sinogram-domain ROI is two, whereas in FIG. 9 the ratio between pixel pitches inside and outside the sinogram-domain ROI is four. The coarse-resolution pixels outside the ROI (i.e., the white region) have the respective resolutions shown in the upper left corner of the grids shown in FIGS. 8 and 9, whereas the pixels with the ROI (i.e., the grey region) have the smaller resolution represented by the grid. In FIGS. 8 and 9, the boundary of the sinogram-domain ROI is selected to eliminate all overlap between the coarse-resolution pixels and the projection of the image-domain ROI.

Alternatively, the boundary of the sinogram-domain ROI can be chosen to instead exclude only those coarse-resolution pixels overlapping with the projection of the image-domain ROI by more than a predefined ratio.

In certain implementations, voxels inside the image-domain ROI are assigned a predefined value (e.g., the value 1) and regions outside the image-domain ROI are assigned another predefined value (e.g., the value 0). Then the sinogram-domain ROI can be determined to include only those pixels whose forward projection value lies within a predefined range of values (e.g., greater than zero, one, or ten).

The pixel values of the projection data within the sinogram-domain ROI can be obtained using, e.g., the projection data with the native resolution of the X-ray detectors. Thus, multiresolution projection data can be generated.

FIG. 5 shows a flow diagram of one implementation of step 140.

In step 510 of step 140, the image-domain HF-ROI (i.e., the image-domain ROI) is forward projected to generate the HF-ROI projections (i.e., projection of the image-domain ROI).

In step 520 of step 140, coarse-resolution pixels having a predefined overlap ratio with the HF-ROI projections are identified as being the part of the project HF ROI (i.e., the sinogram-domain ROI).

In step 530 of step 140, a grid for the projection data is determined having a high-resolution pixel pitch in the sinogram-domain ROI. Then, the projection data within sinogram-domain ROI is populated to have a resolution commensurate with this high-resolution pixel pitch, e.g., using the projection data having the native detector resolution.

In step 150 of method 100, the resolution of the ROI in the image domain is refined by performing an IR method using the multiresolution projection data. The system-matrix equation for multiple resolution data can be split into low- and high-resolution parts, as represented by $$\begin{bmatrix} A_{H,H} & A_{L,H} \\ A_{H,L} & A_{L,L} \end{bmatrix} \begin{bmatrix} f_H \\ f_L \end{bmatrix} = \begin{bmatrix} g_H \\ g_L \end{bmatrix},$$

wherein $f_H$ is the reconstructed image having a higher resolution and being inside the image-domain ROI, $f_L$ is the reconstructed image having a lower resolution and being outside the image-domain ROI, $g_H$ is the projection data having a higher resolution and being within the sinogram-domain ROI, and $g_L$ is the projection data having a lower resolution and being outside the sinogram-domain ROI.

In certain implementations, iterations to optimize the high- and low-resolution reconstructed images can be performed separately, and, once the low-resolution reconstructed image converges to a stable solution, the low-resolution reconstructed image can be maintained constant while the IR method continues to optimize the high-resolution reconstructed image inside the ROI. For example, the isolated low-resolution image reconstruction problem can be expressed as $$\begin{bmatrix} A_{L,H} \\ A_{L,L} \end{bmatrix} f_L = \begin{bmatrix} g'_H \\ g'_L \end{bmatrix},$$

wherein $g'_H = g_H - A_{H,H} f_H$ and $g'_L = g_L - A_{H,L} f_H$ and the high-resolution image $f_H$ is held constant. Additionally, the isolated low-resolution image reconstruction problem can be expressed as $$\begin{bmatrix} A_{H,H} \\ A_{H,L} \end{bmatrix} f_H = \begin{bmatrix} g''_H \\ g''_L \end{bmatrix},$$

wherein $g''_H = g_H - A_{L,H}f_L$ and $g''_L = A_{:,L}f_L$ and the low-resolution image $f_L$ is held constant. Further, different regularization terms can be used for the low- and high-resolution image $f_L$ and $f_H$. Any known method can be used to optimize the corresponding objective functions with their corresponding data-fidelity and regulation terms.

In certain implementations, the data-fidelity or regulation terms can operate as a constraint, rather than an optimization term.

In certain implementations, the minimization of the objective function combining both high- and low-resolution images can be given by $$\underset{f_L, f_H}{\arg\min} \varphi_{Total}(f_L, f_H)$$

wherein the total objective function is given by $$\varphi_{Total} = \left( \begin{bmatrix} A_{H,H} & A_{L,H} \\ A_{H,L} & A_{L,L} \end{bmatrix} \begin{bmatrix} f_H \\ f_L \end{bmatrix} - \begin{bmatrix} g_H \\ g_L \end{bmatrix} \right)^T \left( \begin{bmatrix} A_{H,H} & A_{L,H} \\ A_{H,L} & A_{L,L} \end{bmatrix} \begin{bmatrix} f_H \\ f_L \end{bmatrix} - \begin{bmatrix} g_H \\ g_L \end{bmatrix} \right) + \beta_H U_H(f_H) + \beta_L U_L(f_L),$$

$U_H(f_H)$ is the regularization function for the high-resolution image, $U_L(f_L)$ is the regularization function for the low-resolution images, T represent the matrix transpose, and $\beta_H$ and $\beta_L$ are respective regularization constants applying relative weights to the regularization terms in the objective function.

In certain implementations, the high- and low-resolution regularization function can be the same, and can even be unified into a single function. Any known regularization function can be used.

In certain implementations, separate high- and low-resolution objective functions can be minimized, and the IR method can iterate between optimizing the high- and low-resolution objective functions. Also, after a stable solution has been obtained for the low-resolution image, then the high-resolution objective function can be optimized independently. The high-resolution objective function can be given by $$\varphi_H = \left( \begin{bmatrix} A_{H,H} \\ A_{H,L} \end{bmatrix} f_H - \begin{bmatrix} g''_H \\ g''_L \end{bmatrix} \right)^T \left( \begin{bmatrix} A_{H,H} \\ A_{H,L} \end{bmatrix} f_H - \begin{bmatrix} g''_H \\ g''_L \end{bmatrix} \right) + \beta_H U_H(f_H).$$

The low-resolution objective function can be given by $$\varphi_L = \left( \begin{bmatrix} A_{L,H} \\ A_{L,L} \end{bmatrix} f_L - \begin{bmatrix} g'_H \\ g'_L \end{bmatrix} \right)^T \left( \begin{bmatrix} A_{L,H} \\ A_{L,L} \end{bmatrix} f_L - \begin{bmatrix} g'_H \\ g'_L \end{bmatrix} \right) + \beta_L U_L(f_L).$$

Figure 6:
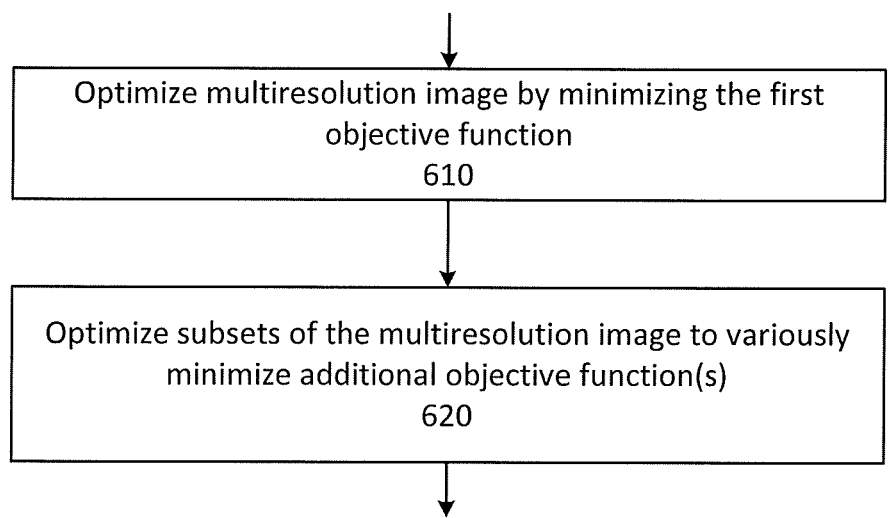
FIG. 6 shows a flow diagram of a step to reconstruct/refine a multiresolution image using different resolutions (i.e., pixel pitches) inside and outside of the ROIs in the image domain, according to one implementation.

FIG. 6 shows a flow diagram of one implementation of step 150.

In step 610 of step 150, the multiresolution image is optimized by minimizing a first objective function, or a combination of objective functions. For example, $\varphi_{Total}$ can be minimized for a predefined number of iterations or until the low-resolution image has satisfied a convergence criteria and stabilized. Alternatively, the combination of $\varphi_H$ and $\varphi_L$ can be minimized iteratively to satisfy a predefined convergence criterion. In certain implementations, only $\varphi_L$ is minimized in step 610.

In step 620 of step 150, the multiresolution image is further refined by minimizing one or more additional objective functions. For example, $\varphi_H$ can be minimized independently.

Alternatively, a new sub-ROI can be defined with a smaller pixel pitch than the ROI, and a new objective function for the sub-ROI can be minimized while holding all other regions outside the sub-ROI constant.

Further, in certain implementations, multiple ROIs and resolutions are possible, and each ROI can have its own corresponding objective function. Then, the objective functions for each of these ROIs can be minimized, either in parallel or serially, as discussed above.

Generally, iterative reconstruction using multiple resolutions for the image and the projection data can be viewed as blending separate iterative reconstructions each involving different resolutions for the images in respective ROIs and for the projection data in respective ROIs. The above description can also be straightforwardly extended to the case of more than two resolutions and/or more than one ROI with high resolution, as would be understood by a person of ordinary skill in the art. Moreover, the parameters applied in the IR method can be tuned separately for each ROI by treating each ROI as a separate reconstruction problem with its own unique image, projection data, and resolution.

Implementation of ray-driven forward projection can be achieved by calculating the contribution of the respective voxels along a given ray incident on a given pixel by determining the overlap between the ray and the respective voxels. Thus, the relative contribution to the ray integral depends on the size/resolution of the respective voxels through which it passes (e.g., a high-resolution voxel will be smaller and contribute proportionately less, but this is offset by the fact that the number of high-resolution voxels will be proportionately greater, such that the contribution as a function of length is conserved).

Similarly, the pixel-driven back-projections, which represent the contribution of the pixels to the respective voxels, will also depend on the size/overlap of the voxels and pixels represented by terms represented by respective matrix elements of the back-projection operation, as would be understood by a person of ordinary skill in the art. Thus, for the implementation of the pixel-driven backprojection, each voxel in an image ROI is back-projected in accordance with the volume of rays from the X-ray source to the respective pixels (e.g., this volume will be roughly proportional to the cross-sectional area of the corresponding pixel).

Returning to FIG. 1, in step 155 of method 100, an inquiry is performed whether the stopping criteria have been satisfied. If the stopping criteria have not been satisfied, method 100 proceeds from step 155 to step 130 and the iterative loop beginning from step 130 and continuing through step 150 is repeated. Otherwise, method 100 is complete.

In certain implementations, when step 130 is repeated, the determination of the FIR ROI is performed on the multiresolution image rather than on the initial image, and a sub-ROI can be defined within the ROI. Thus, ROIs, sub-ROIs, and sub-sub-ROIs can be constructed one upon another in a nested fashion. The stopping criteria can include a resolution criterion that inquires whether features within the ROI might be rendered more sharply by using a smaller pixel pitch, or if a smaller pixel pitch is unlikely to significantly improve the image quality of the multiresolution reconstructed image. For example, this inquiry might be realized using a difference between the forward projection of the multiresolution reconstructed image and the native-resolution projection data. Regions in which the difference is large can indicate that the features in these regions are under resolved, and, during the next iteration, a higher resolution (up to the native resolution) can be applied to these under-resolved regions.

In certain implementations, the stopping criteria can be satisfied when a pixel pitch within the projection data and the multiresolution image reach the native resolution of the X-ray detectors.

In certain implementations, the stopping criteria can also be satisfied when a maximum number of iterations of the IR method is reached.

Method 100 has several advantages over more conventional methods. First, the resolution for regions within the reconstructed image regions can be consistent over iterations of the IR method. Second, parameters used in the IR method can also be consistent over IR iterations. This contrasts with the two-pass ROI IR method, for example, in which a different set of IR parameters is needed when the image resolution is changed for the second-pass of the IR method. Third, image information outside an ROI is preserved in the multiresolution image, and can be displayed, albeit with a coarser resolution, to provide context for the anatomy displayed in the ROI. Fourth, the computing overhead for image/data outside the ROI is significantly reduced. Fifth, multiple ROIs with different resolutions can be reconstructed. Sixth, truncation artifacts can be minimized even when the ROI is much smaller than the attenuating object OBJ.

Now exemplary clinical applications and implementations are provided of the multiresolution image reconstruction method using both multiresolution representations in the image and sinogram domains.

In certain implementations, IR algorithms are used in clinical computed tomography (CT). For example, IR algorithms have demonstrated advantages in clinical applications by reducing radiation dose and improving image quality. For example, in rotational C-arm cone-beam CT (CBCT) for interventional procedures, three-dimensional imaging features such as low-contrast imaging (LCI, which can also be referred to as CT-like imaging) and three-dimensional digital subtraction angiography (3D-DSA) can benefit from the advantages of reconstructing images using an IR algorithm to improve image quality and to reduce artifacts. With rapid advances in GPU technology, the computational time required to generate an IR image has been significantly reduced to the point of becoming clinically feasible during interventional procedures. This is significant because, for interventional procedures, information is needed to be rapidly available if it is to be useful for guiding decisions for clinical procedures. Unlike clinical CT, C-arm CBCT equipped with a flat-panel detector (FPD) is designed to conduct 2D imaging and to be flexible and mobile in order to rotate to convenient angles in an operation room. Further, an FPD usually has a smaller field of view (FOV) relative to a typical CT detector, and FPDs typically have higher detector resolution suitable for high-resolution imaging. Therefore, CT reconstructed images obtained using the combination of an IR algorithm with C-arm CBCT using an FPD has not been used in the interventional applications because the computational time for image reconstruction would be too long to be clinically relevant. This long computational time results from the combination of the FOV and the high-resolution of the detectors. Nevertheless, if the computational times for image reconstruction can be reduced, this combination can be advantageous. The methods described herein provide a path whereby images with high resolutions in the regions of interest can be generated within a clinically relevant time frame by sacrificing resolution outside of the ROIs in order to generate a multiresolution image using an IR algorithm.

Figure 10:
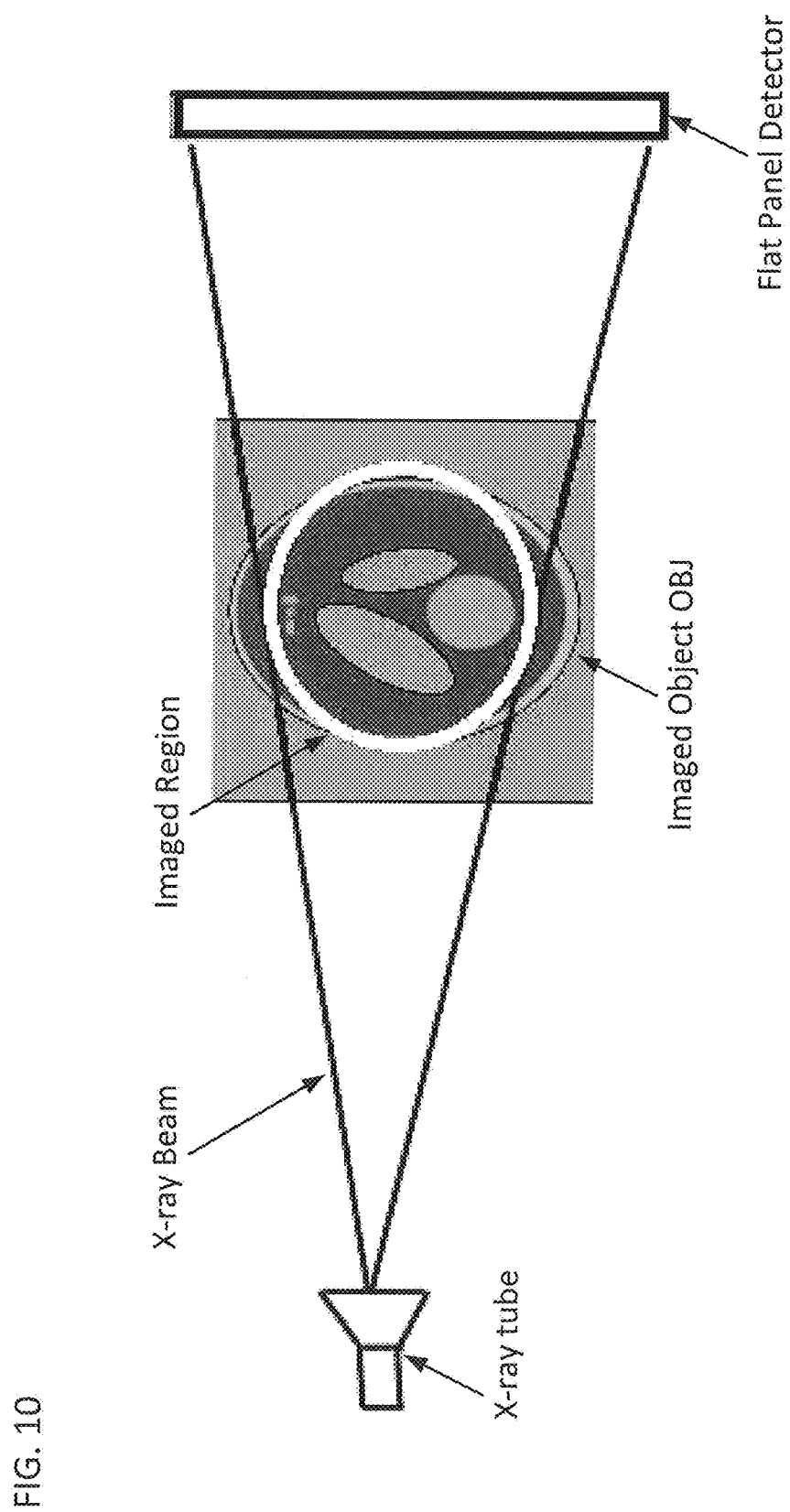
FIG. 10 shows a diagram of an X-ray projection measurement onto a flat panel detector (FPD), according to one implementation.

FIG. 10 shows an example of acquiring a projection image using a small FPD. Thus, the imaged object OBJ is larger than the imaged region, which is shown as a white circle superimposed on imaged object OBJ. Using a small image volume creates a potential for truncation artifacts in a reconstructed image due to the attenuation of the projection data arising from portions of the object OBJ outside of the imaged region. The smaller size of the FPD can result in data truncation during data acquisition for three-dimensional reconstruction. This is illustrated in FIG. 10 representing an X-ray acquisition using an FPD. For some projection angles, the acquisition FOV fails to completely span the object OBJ, such that data that would make it possible to perfectly characterize the object OBJ is missing due to the limited extent of the FPD. The missed data will reduce the amount of known projection data g available to reconstruct the image based on the system-matrix equation $Af \cong g$ (e.g., IR algorithms can be understood as iterative algorithms to solve this system-matrix equation). When the FOV includes less than the entire object OBJ, the system-matrix equation tends to be underdetermined. That is, as a result of the system-matrix being modeled using a forward projection A, the image inside the FOV is more constrained by the equations than the image outside FOV. Accordingly, the image inside FOV tends to converge to the true solution, while an image outside FOV tends to diverge away from the true solution since its solution space is huge as a result of not being constrained by the system-matrix equation as a result of incomplete projection data.

For clinical applications, the imaged region for reconstruction limits what can be displayed, and, as described above, a small FOV can result in a small imaged region, especially for filtered back-projection (FBP) reconstruction. However, whereas FBP constrains the imaged region, the imaged region can be larger when an IR algorithm is used. The IR algorithm can minimize the least square of the system-matrix equation (e.g., the data fidelity term), which can encompass a larger imaged region than the imaged region used for FBP. Accordingly, the IR algorithm can use a larger image volume, which encompasses the entire object OBJ, in order to reach a solution as close as possible to accurately representing the object OBJ without artifacts due to truncation.

As a result of using a larger imaging region, more voxels are used, resulting in a greater number of image variables in the reconstructed image $f$. Further, truncation correction such as extrapolation on the projection data can be appended to the boundaries of projection data g, to extrapolate projection data representing the entire object OBJ, which would also increase the dimension of the problem by increasing the number of pixels in the projection data g. Even a small increase (e.g., a 30% increase) in the length r of each dimension of the imaged region and a small increase (e.g., a 20% increase) in the length l of each dimension of the projection data can cause a substantial increase in the size of the system matrix problem and the corresponding computational time (e.g., the computational time is of order $O(r^3 \times l^2)$ such that a 30% increase in r and a 20% increase in l results in a 216% increase in the time, i.e., $1.3^3 \times 1.2^2 = 3.16$). Thus, increasing the size of the reconstructed image and projection data without changing their respective resolutions (i.e., pixel pitches) can dramatically increase the image-reconstruction time, potentially making the expanded image regions unsuitable for certain clinical applications such as interventional imaging, which benefits from rapid image reconstruction. The ratios of a 30% increase in the volume length and 20% increase in the projection length are representative of practice for using an IR algorithm for a head scan in a neuro interventional procedure. Thus, without the time savings achieved through the multiresolution IR methods described herein, even a small increase of the dimensions in image and projection domains results in a substantial increase of the IR computational time, causing this computational time to balloon beyond acceptable bounds for various clinical applications.

Figure 11A:
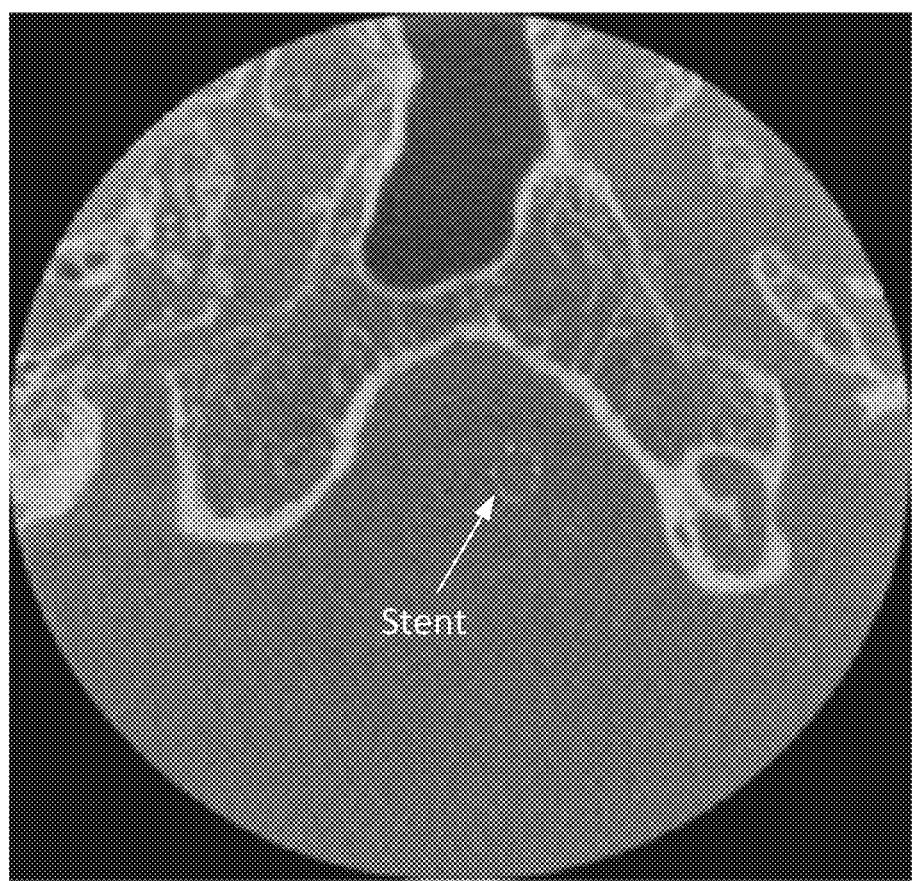
FIG. 11A shows a cross-sectional view of a reconstructed image of a stent being used in an interventional clinical application.
Figure 11B:
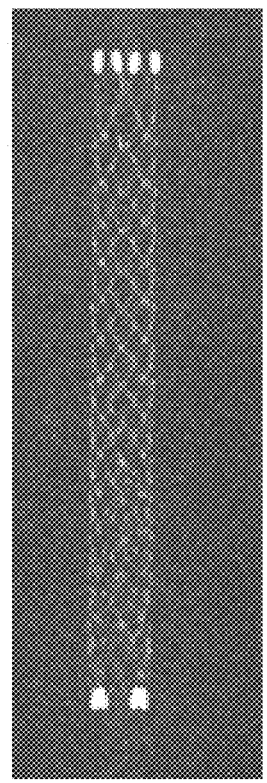
FIG. 11B shows a projection image of a side view of the stent.

Neuro interventional procedures of deploying a stent in a blood vessel is one example of clinical CT imaging in which it is beneficial to use the method described herein in order to achieve fast image reconstruction using an IR algorithm including both high-resolution and low-resolution regions. For example, FIGS. 11A and 11B illustrate a neuro interventional procedure for the placement of a stent using a CT image of a head. FIG. 11A shows a reconstructed image of a cross-section of a head including a circular cross-section of a stent. FIG. 11B shows a side view of the stent with markers at the top and bottom. This stent has diameter of around 3 to 4 mm and length 20 to 30 mm.

As discussed above, in addition to LCI in three-dimensional imaging, C-arm CBCT using a FPD is also capable of high-resolution imaging. However, three-dimensional imaging represents an expansion of more conventional uses of FPD, which was originally designed for two-dimensional imaging for devices such as guide wires, catheters, and stents. The native resolution of FPD is conventionally less than 200 micrometers. Because of this high resolution, in ordinary circumstances the high-resolution imaging in C-arm CBCT with FPD is limited to a small region in order to avoid overburdening the CPU with intensive computation for reconstruction of the image and greatly increasing the image reconstruction time.

A typical high-resolution application for neuro interventional procedure is imaging the stent as in FIGS. 11A and 11B to monitor the stent's placement. A stent is deployed inside a vessel and expanded against vessel walls. Proper execution of this procedure requires that the struts of the stent have complete apposition against to the vessel walls to prevent the stent from sliding out of position. FIG. 11A shows region of interest (ROI) reconstruction using FBP. The cross-section of the stent can be recognized as being a circular shape near the center of FIG. 11A. FIG. 11B shows a side view of the stent, which has a shape of a circular tube.

Figure 12:
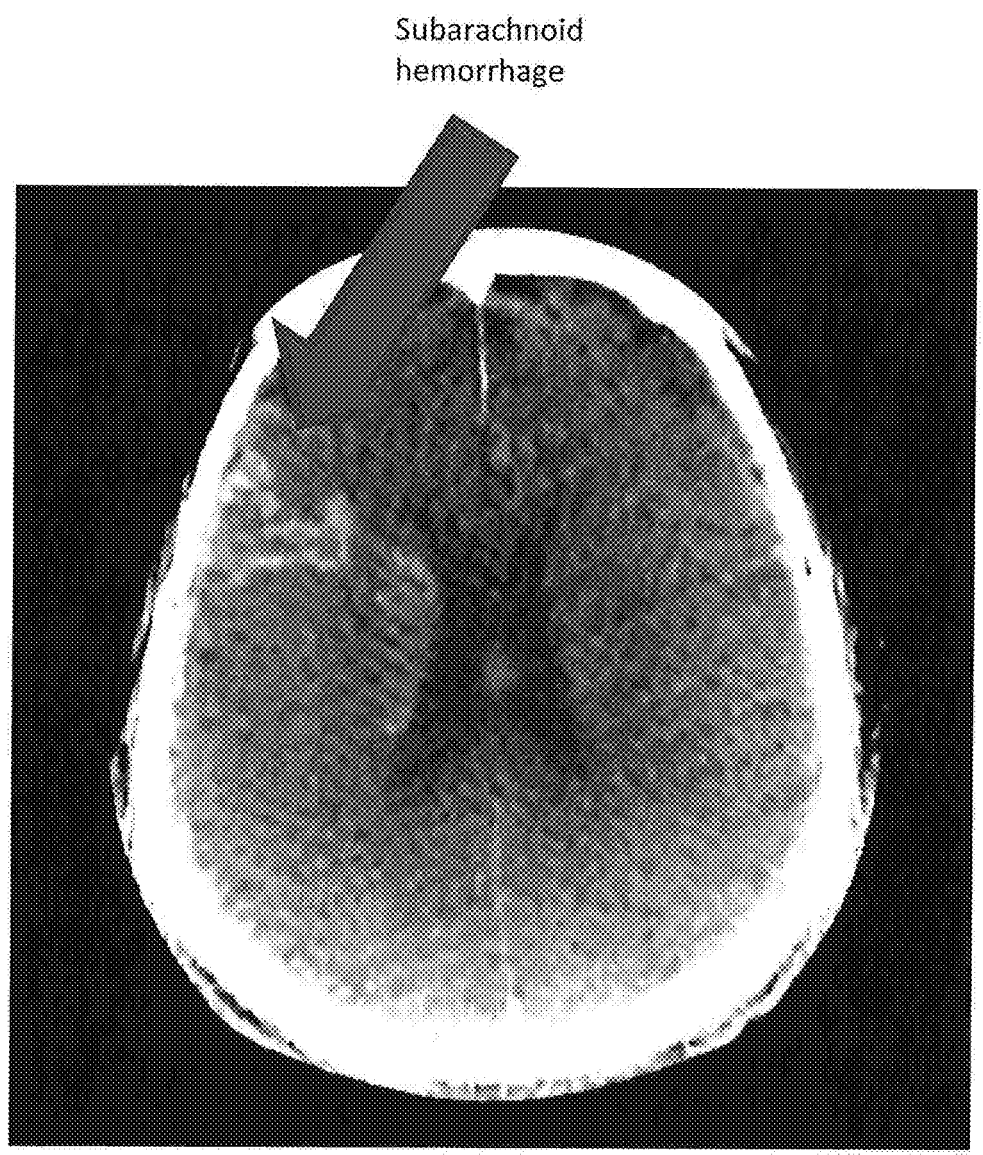
FIG. 12 shows an example of a reconstructed image of a head exhibiting a subarachnoid hemorrhage in a space between the brain cortex and the cranium.

Another clinical application benefiting from the combination of improved speed and localized high-resolution of a multiresolution method is the treatment of a subarachnoid hemorrhage, as shown in FIG. 12. This application is benefited by having a ROI with high-resolution in order to better resolve and differentiate among tissues, such as bleeding chunks, and bones. FIG. 12 shows an image of bleeding into the subarachnoid space surrounding the brain cortex. This phenomenon is called a subarachnoid hemorrhage (SAH). When the subarachnoid space between the brain cortex and cranium is very small, the region in the image representing the bleeding can blend in with the bone, especially if the image resolution is insufficient to resolve the space between the blood and the bone. LCI using the above-described three-dimensional imaging features is usually designed to create a good contrast-to-noise image but at a single lower resolution. The multiresolution image methods described herein can overcome the limitations of the conventional single resolution image generated in LCI. Thus, a multiresolution image would be helpful to increase the resolution images along the edge of the cranium in order to better resolve and differentiate the SAH region between brain cortex and cranium.

As discussed above, C-arm CBCT with FPD usually has a smaller imaging FOV and is equipped with high-resolution imaging capability. Fast image reconstruction is beneficial in order to achieve reasonable reconstruction time in order that the results will be useful and adopted by clinical practitioners in the field. However, reconstructing an image that is uniformly at the native resolution of the FPD could result in a clinically unfeasible increase to the IR reconstruction time. Accordingly, a fast multiresolution IR algorithm is adopted to generate a multiresolution image in which only certain ROIs are reconstructed at a high resolution and the remaining regions are reconstructed at a low-resolution to conserve computational resources.

According to one implementation, the reconstruction problem can be formulated as an IR method that minimizes an objective function including a low-resolution image representing a background (e.g., everything except the ROI) and a high-resolution image representing the ROI. The data fidelity term represents the system-matrix equation $Af \cong g$ bifurcated into high-resolution and low-resolution parts in the image domain:

$$A\begin{bmatrix} f_H \\ f_L \end{bmatrix} = g.$$

Further, as discussed above the sinogram (projection) domain is also bifurcated into high-resolution and low-resolution parts, as demonstrated by the system-matrix equation $$A\begin{bmatrix} f_H \\ f_L \end{bmatrix} \cong \begin{bmatrix} g_H \\ g_L \end{bmatrix}.$$

The insights informing the use of multiple resolutions in the sinogram (projection) include the following two observations. First, it can be observed that the coarse projection data outside of the re-projected ROI does not contribute to the high-resolution ROI in the image domain. Second, it can be observed that projection extrapolation for truncation correction is used to provide a smooth transition of truncated projection boundary, and does not need to be represented at a high-resolution. Accordingly, in the context of the IR algorithm, multiple resolutions in projection data can be used without sacrificing information of clinical significance.

The extension of a single-resolution IR method to a multiresolution IR method, which uses multiple resolutions in the sinogram (projection) domain, can be understood as a partitioning of a single reconstruction problem into multiple inter-related reconstruction problems, each having its own resolution. This extension is realized using the fact that, for each partitioned sub-problem corresponding to a single-resolution and for each iteration of the IR algorithm, there is one ray-driven forward-projection operation and one pixel driven back-projection operation. Bifurcating the IR algorithm into multiple regions (e.g., ROIs and regions outside of the ROIs) can be performed by partitioning the forward-projection and back-projection operations of the IR algorithm according to their respective resolutions. The forward-projection and back-projection operations corresponding to the low-resolution regions, which are often more voluminous than the spatially limited ROIs, will be more computationally efficient because of the lower resolution. Accordingly, the multiresolution IR algorithm can reduce computational cost of ray-driven forward-projection operations (i.e., the number of rays depends on the resolution of projection data) without significantly impacting the image quality inside the ROIs.

In certain implementations, the objective function used to implement the multiresolution IR method is expressed by the constrained optimization problem $$\begin{bmatrix} f_H^* \\ f_L^* \end{bmatrix} = \operatorname{argmin}\|f_H\|_{TV} + t\|f_L\|_{TV}, \text{ subject to}$$

$$\left\|A_1 \begin{bmatrix} f_H \\ f_L \end{bmatrix} - g_H\right\|^2 + s^2 \left\|A_2 \begin{bmatrix} f_H \\ f_L \end{bmatrix} - g_L\right\|^2 \le \epsilon^2, \begin{bmatrix} f_H \\ f_L \end{bmatrix} \ge 0,$$

wherein $A_1$ and $A_2$ are constituent system matrices of the system matrix A corresponding respectively to the high- and low-resolution regions in the projection domain, i.e. $A=[A_1\ A_2]$, $\|\cdot\|$ is a Euclidean distance, and t (s) is the ratio between the low-resolution pixel (voxel) size and high-resolution pixel (voxel) size in the image (projection) domain. The multipliers t and s are used to compensate for the effects on resolution diversity to make the parameter tuning consistent, as if image resolution is uniform. This optimization problem can be solved using any known IR techniques and methods. The expression of the optimization problem uses an objective function that differs in some respects from the objective function discussed above. For example, the objective function discussed above minimizes the data fidelity and regularization terms simultaneously, whereas this expression of the optimization problem minimizes the regularization terms subject to constraints on the data fidelity terms and a constraint that the attenuation be non-negative.

Additionally, in certain implementations, the optimization problem could be posed as minimizing the data fidelity terms subject to a constraint on the regularization terms. Also, in certain implementations, the regularization terms could be omitted from the optimization problem.

The selection of high-resolution and low-resolution regions within the multiresolution reconstructed image can depend on which regions need to be resolved into finer details for better, more refined resolution. The selection of high-resolution and low-resolution regions in the projection domain can then flow from the forward projection of the high- and low-resolution regions in the image domain. For example, the resolution (i.e., pixel pitch) of a pixel in the projection domain can correspond to the finest resolution voxel which X-rays incident on the pixel pass through.

Determining the resolution of various regions in the image domain can be achieved using the automated, semi-automated, and user-driven mechanisms described above, including, e.g., displaying an image in a GUI and having the user select regions within the displayed image, edge-detection methods, spatial-frequency threshold methods, signal processing to differentiate regions having predefined characteristics, which are determined to be clinically relevant, and a combination of the above. For example, in an interventional procedure inserting a device, which has predefined attenuation characteristics, a user input can indicate the predefined attenuation characteristics such that an automated algorithm can detect regions having the predefined attenuation characteristics and flag those regions for high-resolution image reconstruction.

For example, high-resolution ROIs can be selected to correspond to regions with abrupt transitions and edges, such as edges presented by interventional devices or anatomical structure such as bones. In addition to applications with just two resolutions, i.e., a high resolution and a low resolution, multiple high-resolution ROIs can be selected, each being characterized by a unique resolution (i.e., pixel pitch). Accordingly, the methods described herein can improve image resolution of LCI images near sharp anatomical edges within a reconstructed image while maintaining a desired contrast to noise ratio (CNR) for soft tissues. For example, in FIG. 12, a higher image resolution is desired near the subarachnoid space between cranium and cortex. The abrupt changes in the attenuation can be used to determine the ROI in which high resolution is desirable, and this change in the attenuation can be detected using one of several methods, including, e.g., edge detection, segmentation, and wavelet, Laplacian, Gaussian, or other multiscale decomposition.

In certain implementations, the high-resolution ROI can be defined using a binary mask image in which a value of one indicates a ROI pixel and a value of zero indicates a non-ROI pixel.

Figure 13:
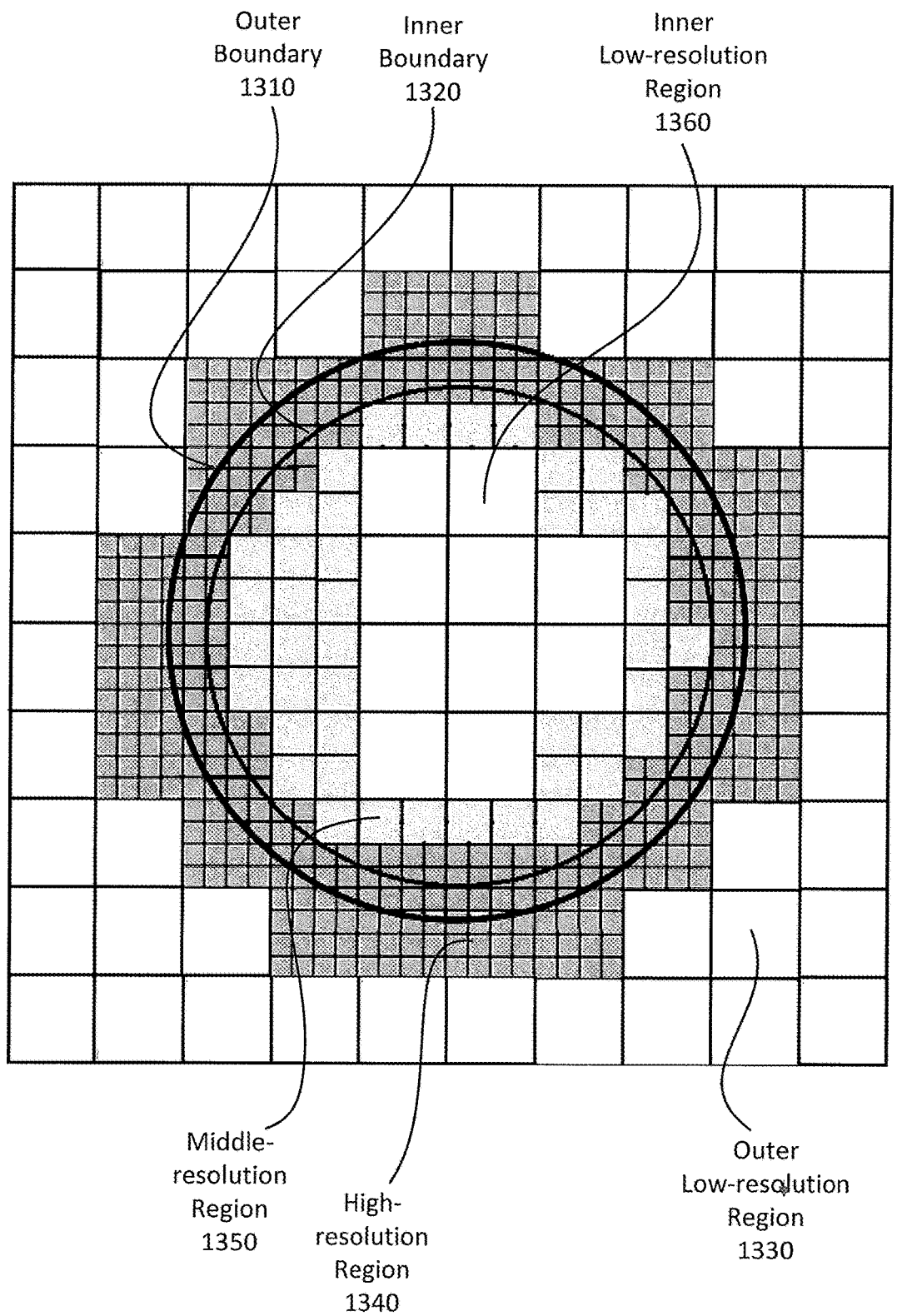
FIG. 13 shows an example of an image being partitioned into four regions of various resolutions, according to one implementation.

FIG. 13 shows a non-limiting example of partitioning an image into four regions: an outer low-resolution region 1330, a middle-resolution region 1350, a high-resolution region 1340, and an inner low-resolution region 1360. In this example, an outer boundary 1310 and an inner boundary 1320 are used to define the high-resolution region. For example, the outer boundary 1310 and the inner boundary 1320 can be respective boundaries of a bone region, such as a cranium, which has sharp features. The high-resolution region 1340 region has a resolution equal to the native resolution of the detectors. The low-resolution regions 1330 and 1360 correspond to parts of the image that are relatively uniform, such as brain tissue. In FIG. 13, the pixel pitch in the low-resolution regions 1330 and 1360 is four times that in the high-resolution region 1340. The middle-resolution region 1350 can include features having a spatial structure with characteristics intermediate between those in the high- and low-resolution regions. In FIG. 13, the middle-resolution region 1350 also functions as a buffer between the high- and low-resolution regions, and has a pixel pitch that is twice that of the high-resolution region 1340.

Figure 14:
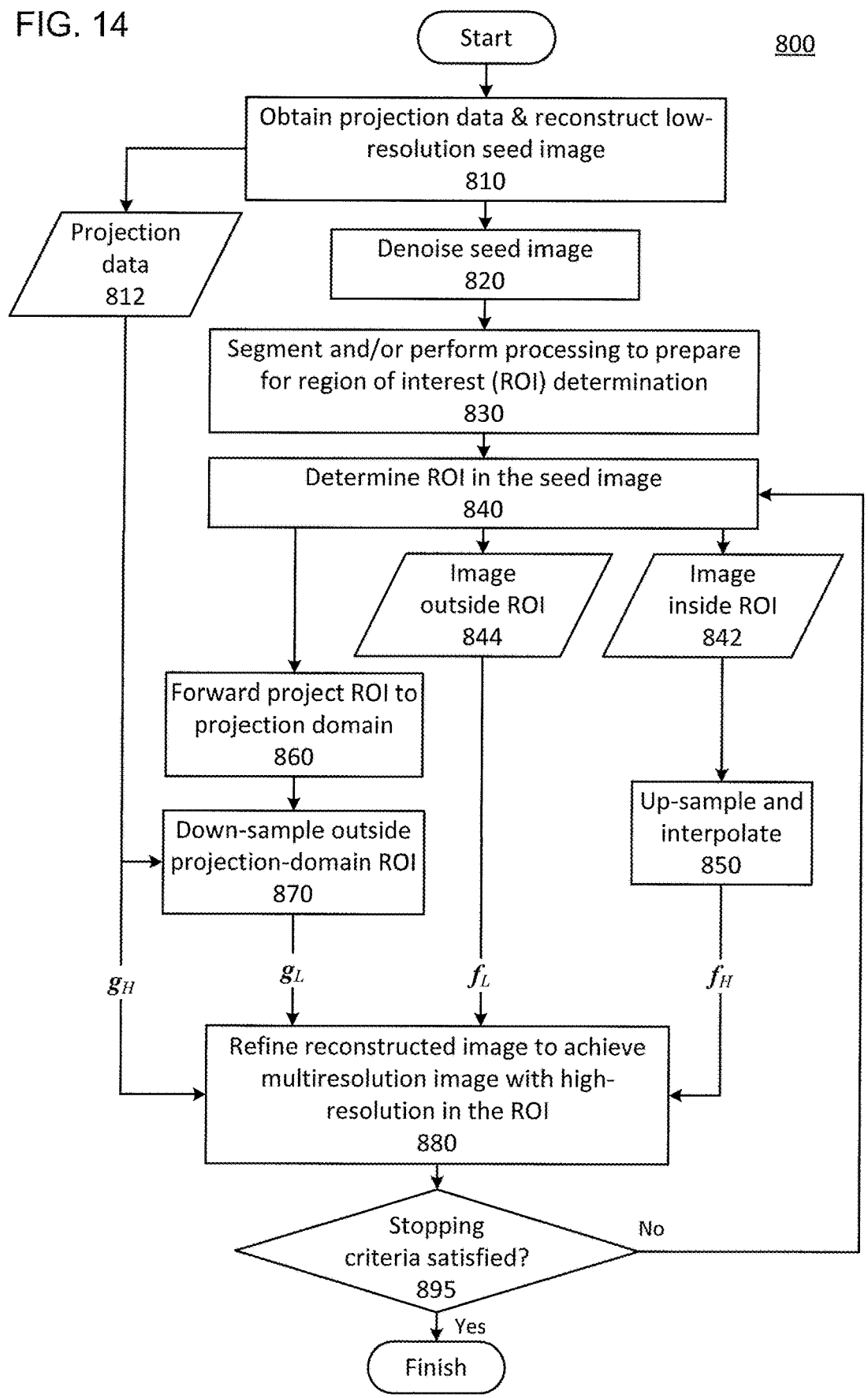
FIG. 14 shows a flow diagram of a second implementation of a multiresolution IR method, according to one implementation.

FIG. 14 shows a flow diagram of method 800 for multi-resolution iterative reconstruction. Method 800 is an alternative implementation to method 100 shown in FIG. 1. Method 800 shows how the projection data and reconstructed image can be partitioned into ROIs, which are addressed uniquely, according to their respective resolutions. In certain implementations of method 800, the multiresolution image and projection data can be automatically partitioned into ROIs.

In step 810 of method 800, the original projection data is obtained at the native resolution of the detectors. The native resolution projection data g 812 can be downsampled to a lower resolution (i.e., a larger pixel pitch corresponding to coarse-resolution pixels) from which a low-resolution seed/initial image is reconstructed. For example, the low-resolution seed image can be reconstructed using FBP or an IR method (with or without iterating to convergence).

In step 820 of method 800, the seed image is denoised, e.g., using linear smoothing filters, anisotropic diffusion, non-local means, or nonlinear filters.

Linear smoothing filters remove noise by convolving the original image with a mask that represents a low-pass filter or smoothing operation. For example, the Gaussian mask comprises elements determined by a Gaussian function. This convolution brings the value of each pixel into closer agreement with the values of its neighbors. In general, a smoothing filter sets each pixel to the average value, or a weighted average, of itself and its nearby neighbors; the Gaussian filter is just one possible set of weights. Disadvantageously, smoothing filters tend to blur an image because pixel intensity values that are significantly higher or lower than the surrounding neighborhood are smeared or averaged across their neighboring area. Sharp boundaries become fuzzy. Generally, local linear filter methods assume that local neighbourhoods are homogeneous, and local linear filter methods, therefore, tend to impose homogeneity on the image obscuring non-homogeneous features, such as lesions or organ boundaries.

Anisotropic diffusion removes noise while preserving sharp edges by evolving an image under a smoothing partial differential equation similar to the heat equation. If the diffusion coefficient were spatially constant, this smoothing would be equivalent to linear Gaussian filtering, but when the diffusion coefficient is anisotropic according to the presence of edges, the noise can be removed without blurring the edges of the image.

A median filter is an example of a nonlinear filter and, if properly designed, a nonlinear filter can also preserve edges and avoid blurring. A median filter operates, for example, by evaluating each pixel in the image, sorting the neighboring pixels according to intensity, and replacing the original value of the pixel with the median value from the ordered list of intensities. The median filter is one example of a rank-conditioned rank-selection (RCRS) filter. For example, median filters and other RCRS filters can be applied to remove salt and pepper noise from an image without introducing significant blurring artifacts.

In addition a filter using a total-variation (TV) minimization regularization term can be used where it is assumed that the areas being imaged are uniform over discrete areas with relatively sharp boundaries between the areas. A TV filter can also be used as another example of a nonlinear filter.

In non-local means filtering, rather than performing a weighted average of pixels according to their spatial proximity, pixels are determined to be a weighted average according to the similarity between patches within the images. Thus, noise is removed based on non-local averaging of all the pixels in an image—not just the neighboring pixels. In particular, the amount of weighting for a pixel is based on the degree of similarity between a small patch centered near that pixel and another small patch centered on the pixel being denoised.

In step 830 of method 800, a seed image can be prepared to determine the ROI in which higher resolution is desirable. These preparations can include the segmentation of the image (e.g., segmenting the bone volumes), edge detection, and/or performing a multiscale decomposition. In certain implementations, a low resolution FBP seed image $f$ is processed using a bone-segmentation and/or an edge detection algorithm, which is performed after denoising the seed image.

In step 840 of method 800, the seed image $f$ is decomposed and partitioned into a low-resolution partition $f_L$, which is outside the ROI, and high resolution partition $f_H$, which is inside the ROI. The low-resolution partition of the seed image $f_L$ can be supplied directly to the proposed multiresolution IR algorithm in step 880 to solve the above optimization problem by minimizing the objective function. Any type of ROI detection algorithm can be applied to determine the ROI. For example, the choice of detection algorithm can depend on the region of the body being imaged, the clinical application, the CT scanner used, and/or user inputs.

In certain implementations, the ROIs can be detected based on predefined features and characteristics using signal processing. The regions which are detected as exhibiting the predefined features and characteristics can then be encompassed by boundary boxes or otherwise enclosed by a three-dimensional surface demarking the boundary of the ROIs.

In step 850 of method 800, the high resolution partition $f_H$ can be upsampled and interpolated to generate a high-resolution image $f_H$ having the desired pixel pitch.

In step 860 of method 800, the ROI is forward projected from the image domain onto the projection domain. This forward projection determining a ROI in the projection domain can be performed using any of the methods described for step 140 of method 100.

For example, a binary mask can be created to represent the ROI in the image domain. The binary mask can have voxels with values of 1 inside the ROI and values of 0 outside the ROI. The ROI in the projection domain can be those pixels for which the forward projection of the binary mask is greater than zero.

Also, step 860 can include extrapolating projection data for regions outside of the measured projection data by forward projecting the seed image. For example, FIG. 10 shows an image in which a projection image does not completely span the imaged object OBJ. However, the edges of the object OBJ not sampled for the projection angle shown in FIG. 10 can be sampled at other projection angles. Therefore, the unsampled regions of object OBJ in FIG. 10 are at least partially represented in the projection data. Accordingly, a reconstructed image can be generated for an expanded imaging region, which is larger than the imaged region shown in FIG. 10, as discussed above. By forward projecting the reconstructed image for this expanded imaging region, projection data can be extrapolated beyond the edges of the FPD shown in FIG. 10, such that the extrapolated projection data completely spans the object OBJ. This extrapolated data can improve the image quality of the multiresolution image by mitigating the truncation effect. This extrapolation can be performed either in step 860 or in step 870.

In step 870 of method 800, the high-resolution or native-resolution projection data is downsampled to generate the low-resolution projection data outside the ROI in the projection domain, which is determined in step 860.

For example, after the projection-domain ROI is determined by forward projecting a binary mask image created from the high-resolution image $f_H$, a second binary mask is created corresponding to the projection-domain ROI. This second binary mask is applied to projection data g 812 that has a native detector resolution, and designates the high-resolution projection data $g_H$ inside of the ROI. In certain implementations, no additional processing is required to the high-resolution projection data $g_H$ because the projection data g 812 is at the desired resolution for the ROI, such that it passes directly to the multiresolution IR algorithm performed in step 880. To generate the low-resolution projection data $g_L$, down-sampling is performed on the native-resolution projection data g 812 outside of the projection-domain ROI, which is designated by the second binary mask to create low-resolution projection data $g_L$.

In certain implementations, the projection data g 812 can be preprocessed data with raw data normalization, beam-hardening correction, scatter correction, and ring artifact correction, for example.

In certain implementations, to improve computational efficiency, the projection data g 812 can be downsampled prior to generating the low-resolution projection data for the reconstruction of the seed image. Then, additional downsampling need not be performed in step 870, and the originally downsampled projection data for the seed image, which is outside the ROI in the projection domain, can be used as the low-resolution projection data $g_L$.

Accordingly, the region outside the image-domain ROI in the image domain, which is the image outside of the ROI 844, is the low-resolution image $f_L$ and can be obtained directly from the seed image without any additional processing. On the other hand, the image inside of the image-domain ROI 842 is initialized by upsampling the seed image and/or interpolating in step 850 to obtain the initial voxel values for the high-resolution image $f_H$. The high-resolution projection data $g_H$ are those projection data inside the projection-domain ROI. The low-resolution projection data $g_L$ are generated in step 870 by down-sampling the projection data inside the projection-domain ROI. Thereby, the low and high-resolution seed images $f_L$ and $f_H$ and the low- and high-resolution projection data $g_L$ and $g_H$ are obtained and supplied to step 880 for reconstructing the multiresolution image by solving the optimization problem discussed above.

In step 880 of method 800, the low- and high-resolution seed images $f_L$ and $f_H$ and the low- and high-resolution projection data $g_L$ and $g_H$ are used to iteratively reconstruct a multiresolution image by optimizing the arguments of the above-described objective function subject to the above described constraints.

In certain implementations, during the optimization of the multiresolution IR problem, $f_L$ and $f_H$ are iteratively and simultaneously updated in each iteration until convergence in order to obtain the optimal images $$\begin{bmatrix} f_H^* \\ f_L^* \end{bmatrix}.$$

In certain implementations during the optimization of the multiresolution IR problem, $f_L$ and $f_H$ are iteratively updated simultaneously in each iteration until the low-resolution image $f_L$ stabilizes. Then, the low-resolution image $f_L$ is held constant while the high-resolution image $f_H$ is iteratively updated to the obtain optimal images $$\begin{bmatrix} f_H^* \\ f_L^* \end{bmatrix}.$$

In certain implementations, the seed image is initially iteratively reconstructed to convergence. Then, during the optimization of multiresolution IR problem, the low-resolution image $f_L^*$ is obtained from the seed image and is held constant while the high-resolution image $f_H$ is iteratively updated to obtain the optimal images $$\begin{bmatrix} f_H^* \\ f_L^* \end{bmatrix}.$$

In step 895 of method 800, an inquiry is performed as to whether the stopping criteria have been satisfied. If the stopping criteria are satisfied, then method 800 is complete. Otherwise, method 800 repeats the steps of determining a ROI and further refining the resolution in the ROI by returning to step 840. The stopping criteria can include whether additional regions would be improved by further refining the resolution.

If the stopping criteria are not satisfied then another ROI can be determined and the resolution within this other ROI can be refined by returning to step 840 of method 800.

In certain implementations, method 800 can proceed from step 895 to step 830, rather than proceeding directing to step 840.

Also, in certain implementations, if the high-resolution projection data has not yet reached the native resolution of the X-ray detector array, then repeating steps 840, 850, 860, and 870 can include using a smaller pixel pitch for the high-resolution image and projection-domain ROIs.

Figure 15:
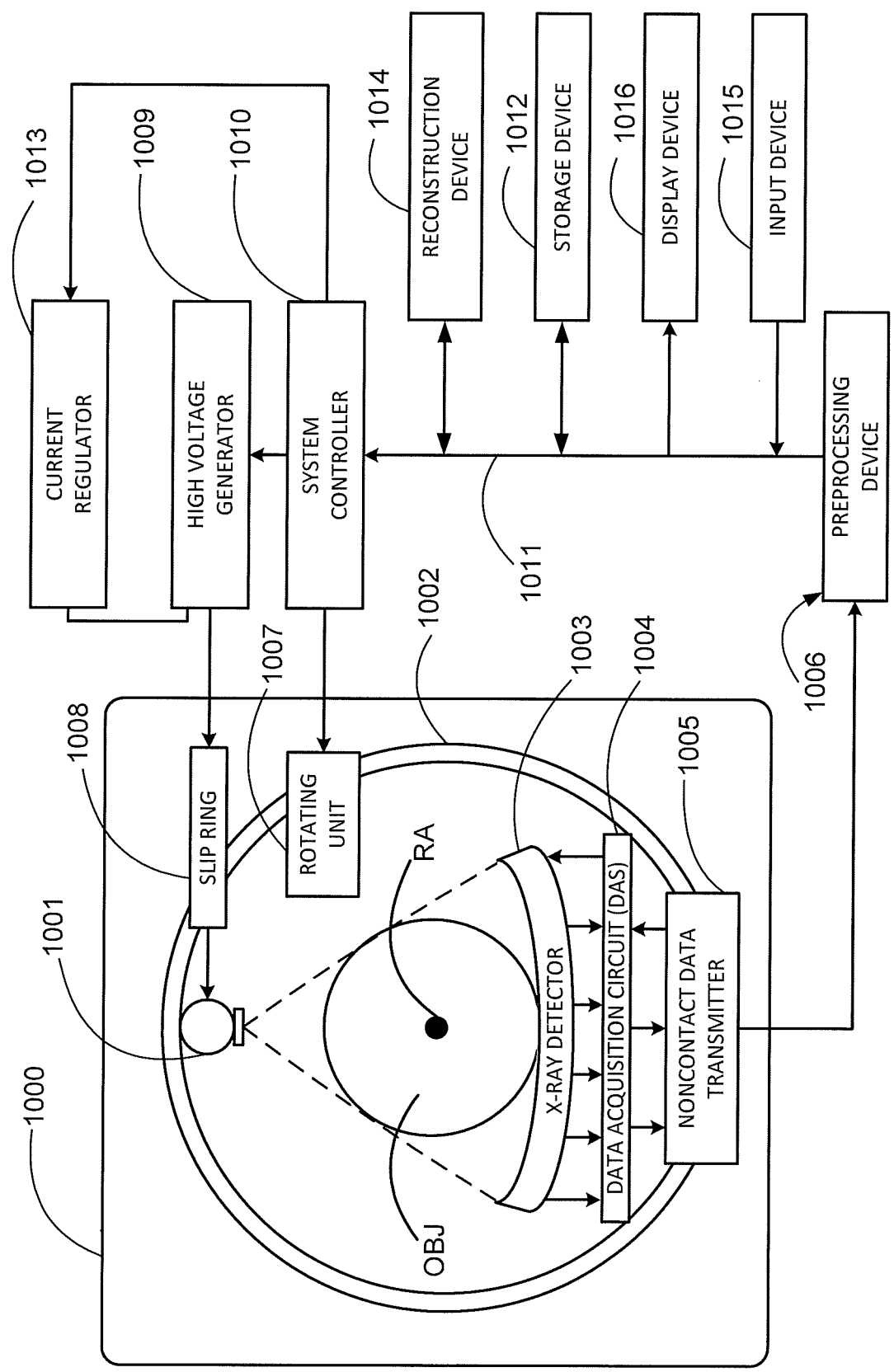
FIG. 15 shows a schematic of an implementation of a CT scanner.

FIG. 15 illustrates an implementation of the radiography gantry included in a CT apparatus or scanner. As shown in FIG. 15, a radiography gantry 1000 is illustrated from a side view and further includes an X-ray tube 1001, an annular frame 1002, and a multi-row or two-dimensional-array-type X-ray detector 1003. The X-ray tube 1001 and X-ray detector 1003 are diametrically mounted across an object OBJ on the annular frame 1002, which is rotatably supported around a rotation axis RA. A rotating unit 1007 rotates the annular frame 1002 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 1009 that generates a tube voltage applied to the X-ray tube 1001 through a slip ring 1008 so that the X-ray tube 1001 generates X-rays. The X-rays are emitted towards the object OBJ, whose cross sectional area is represented by a circle. For example, the X-ray tube 1001 having an average X-ray energy during a first scan that is less than an average X-ray energy during a second scan. Thus, two or more scans can be obtained corresponding to different X-ray energies. The X-ray detector 1003 is located at an opposite side from the X-ray tube 1001 across the object OBJ for detecting the emitted X-rays that have transmitted through the object OBJ. The X-ray detector 1003 further includes individual detector elements or units.

The CT apparatus further includes other devices for processing the detected signals from X-ray detector 1003. A data acquisition circuit or a Data Acquisition System (DAS) 1004 converts a signal output from the X-ray detector 1003 for each channel into a voltage signal, amplifies the signal, and further converts the signal into a digital signal. The X-ray detector 1003 and the DAS 1004 are configured to handle a predetermined total number of projections per rotation (TPPR).

The above-described data is sent to a preprocessing device 1006, which is housed in a console outside the radiography gantry 1000 through a non-contact data transmitter 1005. The preprocessing device 1006 performs certain corrections, such as sensitivity correction on the raw data. A memory 1012 stores the resultant data, which is also called projection data at a stage immediately before reconstruction processing. The memory 1012 is connected to a system controller 1010 through a data/control bus 1011, together with a reconstruction device 1014, input device 1015, and display 1016. The system controller 1010 controls a current regulator 1013 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1001 and the X-ray detector 1003 are diametrically mounted on the annular frame 1002 and are rotated around the object OBJ as the annular frame 1002 is rotated about the rotation axis RA. In the fourth-generation geometry system, the detectors are fixedly placed around the patient and an X-ray tube rotates around the patient. In an alternative embodiment, the radiography gantry 1000 has multiple detectors arranged on the annular frame 1002, which is supported by a C-arm and a stand.

The memory 1012 can store the measurement value representative of the irradiance of the X-rays at the X-ray detector unit 1003. Further, the memory 1012 can store a dedicated program for executing method 100.

The reconstruction device 1014 can execute method 100. Further, reconstruction device 1014 can execute pre-reconstruction processing image processing such as volume rendering processing and image difference processing as needed.

The pre-reconstruction processing of the projection data performed by the preprocessing device 1006 can include correcting for detector calibrations, detector nonlinearities, and polar effects, for example. Further, the pre-reconstruction processing can include various steps of method 100.

Post-reconstruction processing performed by the reconstruction device 1014 can include filtering and smoothing the image, volume rendering processing, and image difference processing as needed. The image reconstruction process can implement various steps of method 100. The reconstruction device 1014 can use the memory to store, e.g., projection data, reconstructed images, calibration data and parameters, and computer programs.

The reconstruction device 1014 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 1012 can be non-volatile, such as ROM, EPROM, EEPROM or FLASH memory. The memory 1012 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 1014 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1016. The display 1016 can be an LCD display, CRT display, plasma display, OLED, LED or any other display known in the art.

The memory 1012 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
   circuitry configured to
      obtain projection data representing an intensity of radiation detected at a plurality of detector elements,
      downsample the projection data to generate low-resolution projection data;
      reconstruct a low-resolution image using the generated low-resolution projection data;
      select a region within the low-resolution image to generate a first image-domain region of interest (ROI),
      generate a first sinogram-domain ROI using a forward projection of the first image-domain ROI,
      obtain, using the projection data, first ROI projection data representing the intensity of the radiation detected within the first sinogram-domain ROI, wherein the first ROI projection data has a smaller pixel pitch than the low-resolution projection data, and
      reconstruct a multiresolution image having a low-resolution pixel pitch outside the first image-domain ROI and a first pixel pitch inside the first image-domain ROI, wherein the low-resolution pixel pitch is greater than the first pixel pitch.

2. The apparatus according to claim 1, wherein the circuitry is further configured to
   select a second image-domain ROI within the low-resolution image, wherein the second image-domain ROI is disjoint from the first image-domain ROI,
   forward project the second image-domain ROI to generate a second sinogram-domain ROI,
   obtain, form the projection data, second ROI projection data representing the intensity of the radiation detected within the second sinogram-domain ROI, wherein the second ROI projection data has a pixel pitch different than the low-resolution projection data, and reconstruct the multiresolution image having the low-resolution pixel pitch outside the first image-domain region and outside the second image-domain region, having the first pixel pitch within the first image-domain region, and having a second pixel pitch within the second image-domain region, wherein the low-resolution pixel pitch is different than the second pixel pitch.

3. The apparatus according to claim 2, wherein the circuitry is further configured to select the pixel pitch of the second sinogram-domain ROI to be equal to the pixel pitch of the first sinogram-domain ROI, and select the first pixel pitch to be equal to the second pixel pitch.

4. The apparatus according to claim 1, wherein the circuitry is further configured to select a second image-domain ROI within the multiresolution image, wherein the second image-domain ROI overlaps the first image-domain ROI, forward project the second image-domain ROI to generate a second sinogram-domain ROI, obtain, using one of the projection data, the first ROI projection data, and a combination of the projection data and the first ROI projection data, second ROI projection data representing the intensity of the radiation detected within the second sinogram-domain ROI, wherein the second ROI projection data has a smaller pixel pitch than the first ROI projection data, update the first image-domain ROI to exclude the second image-domain ROI, update the first ROI projection data to correspond with the updated first image-domain ROI, and reconstruct another multiresolution image having the low-resolution pixel pitch outside the first image-domain ROI and outside the second image-domain ROI, having the first pixel pitch within a region corresponding to the first image-domain ROI minus the second image-domain ROI, and having a second pixel pitch within the second image-domain region, wherein the low-resolution pixel pitch is greater than the first pixel pitch, and the first pixel pitch is greater than the second pixel pitch.

5. The apparatus according to claim 1, wherein the circuitry is further configured to reconstruct a low-resolution image by one of performing a predefined number of iterations of an iterative reconstruction method, performing iterations of the iterative reconstruction method until a predefined convergence criterion is satisfied, performing a filter back-projection method, and performing a Feldkamp-Davis-Kress method.

6. The apparatus according to claim 1, wherein the circuitry is further configured to select the first image-domain ROI by applying a localized measure of spatial variation within the low-resolution image to generate measure data representing a desirability of higher resolution within respective regions of the low-resolution image, and assigning to the first image-domain ROI those regions within the low-resolution image for which the correspond measure data exceeds a predefined threshold.

7. The apparatus according to claim 6, wherein the circuitry is further configured to select the first image-domain ROI by applying the localized measure of spatial variation, wherein the localized measure is one of a Laplacian-pyramid method, a Gaussian-pyramid method, a wavelet-based method, an edge-detection method, a signal-processing method, and a Fourier transform based method.

8. The apparatus according to claim 6, wherein the circuitry is further configured to select the first image-domain ROI by obtaining a user input, and selecting the first image-domain ROI in accordance with the user input.

9. The apparatus according to claim 1, wherein the circuitry is further configured to reconstruct the low-resolution image, wherein the low-resolution image represents a volume enveloping and including an object positioned within an aperture of a computed tomography scanner, thereby to mitigate truncation effects, and extrapolate projection data at boundaries of the obtained projection data from the plurality of detector elements, when the obtained projection data corresponding projection angles does not span the object, and the extrapolated projection data is included in the low-resolution projection data.

10. The apparatus according to claim 1, wherein the circuitry is further configured to reconstruct the multiresolution image using an iterative-reconstruction method by optimizing a first objective function by performing at least one iteration of the iterative-reconstruction method using the first objective function to generate a first update of the multiresolution image, and optimizing a second objective function by performing at least one iteration of the iterative-reconstruction method starting from the first update of the multiresolution image and using the second objective function to generate a second update of the multiresolution image.

11. The apparatus according to claim 10, wherein the circuitry is further configured to reconstruct the multiresolution image using an iterative-reconstruction method by optimizing the first objective function by adjusting an argument including the multiresolution inside and outside of the first image-domain ROI, and optimizing the second objective function by adjusting an argument including the multiresolution inside of the first image-domain ROI, wherein the multiresolution outside of the first image-domain ROI is maintained constant.

12. The apparatus according to claim 10, wherein the circuitry is further configured to reconstruct the multiresolution image using an iterative-reconstruction method by optimizing the first objective function, which includes a first regularization term, optimizing the second objective function, which includes a second regularization term, and the first regularization term imposes a different type of constraint than the second regularization term.

13. The apparatus according to claim 1, wherein the circuitry is further configured to reconstruct the multiresolution image using an iterative-reconstruction method by optimizing an objective function, the objective function including a data fidelity term representing the multiresolution image inside and outside of the first image-domain ROI, a first regularization term representing a constraint imposed on the multiresolution image inside of the first image-domain ROI, and a second regularization term representing a constraint imposed on the multiresolution image outside of the first image-domain ROI.

14. The apparatus according to claim 13, wherein the circuitry is further configured to reconstruct the multiresolution image using an iterative-reconstruction method by optimizing the objective function including regularization terms subject to a constraint on data fidelity terms.

15. The apparatus according to claim 1, wherein the circuitry is further configured to iteratively reconstruct an updated multiresolution image from the multiresolution image, the updated multiresolution image having nested regions of interest, wherein each nested ROI has a smaller pixel pitch than an immediately surrounding nested ROI, and the updated multiresolution image being iteratively reconstructed by selecting a next nested ROI within a current nested ROI of the updated multiresolution image, forward projecting the next nested ROI to generate a next sinogram-domain ROI, obtaining, from the projection data, next projection data representing the intensity of the radiation detected within the next sinogram-domain ROI, wherein the next projection data has a smaller pixel pitch than a current projection data corresponding to a current sinogram-domain ROI outside of the next sinogram-domain ROI, and updating the multiresolution image to have a pixel pitch inside the next nested ROI corresponding to a pixel pitch of the next sinogram-domain ROI.

16. The apparatus according to claim 1, wherein the circuitry is further configured to downsample the projection data by performing one of partitioning pixels of the projection data the into groups of adjacent pixels, the groups of adjacent pixels corresponding to respective pixels of the low-resolution projection data, and summing pixel values within each group to generate respective values of the low-resolution projection data, partitioning the pixels of the projection data the into the groups of adjacent pixels, the groups of adjacent pixels corresponding to the respective pixels of the low-resolution projection data, and averaging the pixel values within each group to generate the respective values of the low-resolution projection data, and obtaining respective areas of the pixels of the low-resolution projection data, and integrating an interpolation of values of the pixels of projection data within the respective areas of the pixels of the low-resolution projection data to generate the low-resolution projection data.

17. An apparatus, comprising:

an X-ray source configured to transmit X-rays;

a plurality of detector elements arranged diametrically across an aperture of the apparatus to the X-ray source, wherein the plurality of detector elements is configured to generate projection data representing an intensity of the X-rays detected at respective detector elements of the plurality of detector elements, and circuitry configured to obtain projection data representing an intensity of radiation detected at the plurality of detector elements, downsample the projection data to generate low-resolution projection data;

reconstruct a low-resolution image using the low-resolution projection data;

select a region within the low-resolution image to generate a first image-domain region of interest (ROI), generate a first sinogram-domain ROI using a forward projection of the first image-domain ROI, obtain, using the projection data, first ROI projection data representing the intensity of the radiation detected within the first sinogram-domain ROI, wherein the first ROI projection data has a smaller pixel pitch than the low-resolution projection data, and reconstruct a multiresolution image having a low-resolution pixel pitch outside the first image-domain ROI and a first pixel pitch inside the first image-domain ROI, wherein the low-resolution pixel pitch is greater than the first pixel pitch.

18. A method, comprising:

obtaining projection data representing an intensity of radiation detected at a plurality of detector elements, downsampling the projection data to generate low-resolution projection data;

reconstructing a low-resolution image using the low-resolution projection data;

selecting a region within the low-resolution image to generate a first image-domain region of interest (ROI), generating a first sinogram-domain ROI using a forward projection of the first image-domain ROI, obtaining, from the projection data, first ROI projection data representing the intensity of the radiation detected within the first sinogram-domain ROI, wherein the first ROI projection data has a smaller pixel pitch than the low-resolution projection data, and reconstructing a multiresolution image having a low-resolution pixel pitch outside the first image-domain ROI and a first pixel pitch inside the first image-domain ROI, wherein the low-resolution pixel pitch is greater than the first pixel pitch.

19. The method, according to claim 18, further comprising:

iteratively reconstructing an updated multiresolution image from the multiresolution image, the updated multiresolution image having nested regions of interest, wherein each nested ROI has a smaller pixel pitch than an immediately surrounding nested ROI, and the updated multiresolution image being iteratively reconstructed by selecting a next nested ROI within a current nested ROI of the updated multiresolution image, forward projecting the next nested ROI to generate a next sinogram-domain ROI, obtaining, from the projection data, next projection data representing the intensity of the radiation detected within the next sinogram-domain ROI, wherein the next projection data has a smaller pixel pitch than a current projection data corresponding to a current sinogram-domain ROI outside of the next sinogram-domain ROI, and updating the multiresolution image to have a pixel pitch inside the next nested ROI corresponding to a pixel pitch of the next sinogram-domain ROI.

20. A non-transitory computer readable storage medium including executable instruction, wherein the instructions, when executed by circuitry, cause the circuitry to perform the method according to claim 18.

* * * * *